| (12) | United States Patent<br>Ninomiya et al. | (10) Patent No.: US 10,506,995 B2<br>(45) Date of Patent: Dec. 17, 2019 |
|---|---|---|

(54) MOBILE X-RAY IMAGING DEVICE

(71) Applicant: Hitachi, Ltd., Tokyo (JP)

(72) Inventors: Atsushi Ninomiya, Tokyo (JP); Katsumi Usami, Tokyo (JP); Masaru Yokoyama, Tokyo (JP); Kazuyuki Yanase, Tokyo (JP); Kaoru Yamamoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 197 days.

(21) Appl. No.: 15/544,526

(22) PCT Filed: Mar. 17, 2016

(86) PCT No.: PCT/JP2016/058572
§ 371 (c)(1),
(2) Date: Jul. 19, 2017

(87) PCT Pub. No.: WO2016/152740
PCT Pub. Date: Sep. 29, 2016

(65) Prior Publication Data
US 2017/0360386 A1    Dec. 21, 2017

(30) Foreign Application Priority Data

Mar. 23, 2015  (JP) ................................ 2015-060089

(51) Int. Cl.
*A61B 6/00*           (2006.01)
(52) U.S. Cl.
CPC ............ *A61B 6/4405* (2013.01); *A61B 6/547* (2013.01)

(58) Field of Classification Search
CPC ..... A61B 6/4405; A61B 6/547; A61B 6/4452; A61B 17/1703; A61B 50/13
See application file for complete search history.

(56) References Cited

U.S. PATENT DOCUMENTS 4,752,948 A * 6/1988 MacMahon .......... A61B 6/4405
378/193
4,989,229 A * 1/1991 Negrelli ................. A61B 6/105
378/193

(Continued)

FOREIGN PATENT DOCUMENTS

| JP | 5-76406 U | 10/1993 |
|---|---|---|
| JP | 05-76409 U | 10/1993 |

(Continued)

OTHER PUBLICATIONS

International Search Report of PCT/JP2016/058572 dated Jun. 14, 2016.

(Continued)

*Primary Examiner* — David P Porta
*Assistant Examiner* — Fani Boosalis
(74) *Attorney, Agent, or Firm* — Mattingly & Malur, PC

(57) ABSTRACT

Provided is a mobile X-ray imaging device having a foldable arm unit equipped with an X-ray tube unit, and a storage concave for storing the folded arm unit on the front side of a main body. An end of the arm unit fixed to the main body side is made slidable with respect to the main body. With this configuration, it is possible to provide the mobile X-ray imaging device having a high degree of flexibility in arranging the X-ray tube when imaging is performed, and also the forward view is never be obstructed by the device in transit.

17 Claims, 20 Drawing Sheets

(56) References Cited

U.S. PATENT DOCUMENTS

| | | | |
|---|---|---|---|
| 5,265,149 A | 11/1993 | Varisco | |
| 2013/0188781 A1* | 7/2013 | Kaku | A61B 6/4405 |
| | | | 378/197 |
| 2014/0098943 A1* | 4/2014 | Omura | A61B 6/4452 |
| | | | 378/198 |

FOREIGN PATENT DOCUMENTS

| | | |
|---|---|---|
| JP | 2009-201844 A | 9/2009 |
| JP | 2013-146404 A | 8/2013 |
| JP | 2014-138673 A | 7/2014 |
| JP | 2015-043930 A | 3/2015 |

OTHER PUBLICATIONS

International Preliminary Report on Patentability received in corresponding International Application No. PCT/JP2016/058572 dated Oct. 5, 2017.
Japanese Office Action received in corresponding Japanese Application No. 2015-060089 dated Dec. 26, 2017.

* cited by examiner

MOBILE X-RAY IMAGING DEVICE

TECHNICAL FIELD

The present invention relates to a mobile X-ray imaging device equipped with wheels, configured to move to a desired place where imaging is performed, and more particularly, the present invention relates to the mobile X-ray imaging device that ensures a field of vision on the device in transit, as well as enhancing operability.

BACKGROUND ART

A mobile X-ray imaging device is a small-sized X-ray imaging device having an X-ray generator installed on a carriage, moved to a spot where a subject is in, for instance, a patient room, and the subject is placed between an X-ray tube and an X-ray detector which are positioned to face each other, and then imaging is performed. Conventional mobile X-ray imaging devices have a structure that the X-ray tube is connected to a strut installed on the carriage, via a movable supporter such as a pantograph arm, so as to enable imaging in postures at various heights and angles within a spatially limited room, and a main body fixed on the carriage accommodates elements such as a power supply and a controller of the X-ray tube. The main body is configured as a console also provided with an operating unit.

In the mobile X-ray imaging device with such a structure as described above, a handle for moving the device is generally mounted on the main body (console) side. Therefore, when moving the mobile X-ray imaging device, there is a problem that the strut positioned forward of the console is apt to obstruct a view, causing difficulties in ensuring safety while the carriage is traveling.

In general, the X-ray tube is integral with a high voltage generator serving as a drive source of the X-ray tube, together with an aperture unit, resulting in heavy weight. Upon imaging, if this weighty X-ray tube unit is moved according to a movable supporter, balance is lost, i.e., the center of the gravity is off-centered, resulting in that the device is prone to toppling.

In order to solve the foregoing problems of the mobile X-ray imaging device, there have been some suggestions conventionally. By way of example, Patent Document 1 suggests a mobile X-ray imaging device having a structure that a foldable arm unit equipped with an X-ray tube unit on one end thereof is fixed on the forward end of the main body, in rotatable and swiveling manner. This device is provided with a mechanism that limits rotation and swiveling angles of the arm with respect to the end on the main body, thereby preventing toppling of the device.

PRIOR ART DOCUMENT

Patent Document

Patent Document 1
DESCRIPTION of U.S. Pat. No. 5,265,149

DISCLOSURE OF THE INVENTION

Problems to be Solved by the Invention

In the technique disclosed by the Patent Document 1, the movable supporter of the X-ray tube unit comprises two foldable arms, and it is not necessary to provide a high strut on the front side of the main body. However, in order to perform imaging with setting the X-ray tube at a high position, there is a limit to the extent to which the length (height) of each arm can be reduced. In this case, the arm at a position higher than the main body has to be placed forward of the main body, failing to secure sufficient forward view. In addition, a movable range of the X-ray tube made up of two arms, as well as preventing toppling, is limited.

An object of the present invention is to provide the mobile X-ray imaging device that has a high degree of flexibility in arranging the X-ray tube when imaging is performed, and also the forward view will never be obstructed by the X-ray tube of the device in transit. Another object of the present invention is to provide the mobile X-ray imaging device that stabilizes the posture of the device even though the position of the X-ray tube varies when imaging is performed, so as to prevent toppling of the device.

Means for Solving the Problems

In order to achieve the foregoing objects, the mobile X-ray imaging device of the present invention is provided with a foldable arm unit equipped with an X-ray tube unit, and a storage concave for storing the arm unit being folded, in the front side of a main body. In addition, the end of the arm unit fixed on the main body side is made slidable with respect to the main body.

Advantages of the Invention

According to the present invention, the device is moved with the arm unit being stored in the storage concave that is provided on the main body, whereby the forward view of the main body is not obstructed and sufficient visibility can be ensured. In addition, since the end of the arm unit is slidable with respect to the main body, it is possible to enlarge the movable range without elongating the arm unit. With this configuration, the movable range of the X-ray tube can be expanded. Other features and effects of the present invention will be described according to the following embodiments.

BRIEF DESCRIPTION OF THE DRAWINGS

FIG. 7(a) being a plan view and FIG. 7(b) being a side view;

FIG. 8(a) showing the state where the support frame is stored in a main body, and FIG. 8(b) showing the state where the support frame is extracted.

BEST MODE FOR CARRYING OUT THE INVENTION

First Embodiment

A mobile X-ray imaging device of the present embodiment is provided with an X-ray tube unit, a main body configured to accommodate a drive unit of the X-ray tube unit, wheels mounted on the main body, and an arm unit coupling the X-ray tube unit with the main body, and the arm unit includes plural arms being foldable. The main body has a storage concave for storing the arm unit being folded, inwardly from the main body surface.

In the mobile X-ray imaging device of the present embodiment, one end of the arm unit is slidably supported on the storage concave, and the arm unit comprises a first arm and a second arm, one end of the first arm being slidably coupled to the main body, the second arm being foldable with respect to the first arm, and one end of the second arm being fixed to the X-ray tube unit. The other end of the second arm is coupled to the other end of the first arm, in a manner rotatable about the axis orthogonal to the longitudinal direction of the second arm.

The main body of the mobile X-ray imaging device according to the present invention has an inclined plane forward in the traveling direction, and the storage concave is provided on the inclined plane. The inclined plane may have a flat surface, or a curved surface being convex upwardly. If the inclined plane is the curved surface, the arms constituting the arm unit may have a bowed shape along the curved surface of the inclined plane.

Figure 1:
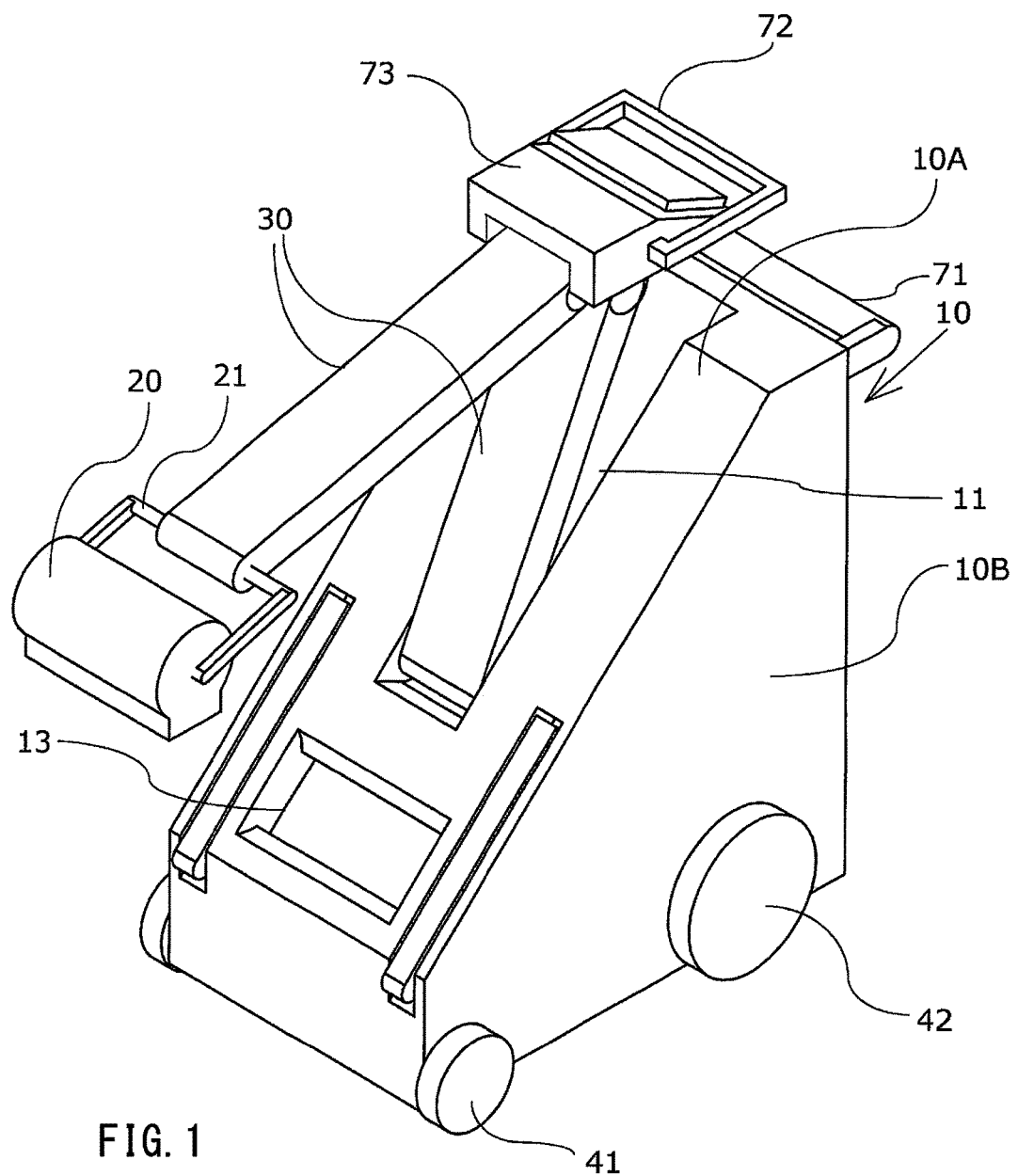
FIG. 1 is a perspective view showing an entire configuration of a mobile X-ray imaging device according to the first embodiment.
Figure 2:
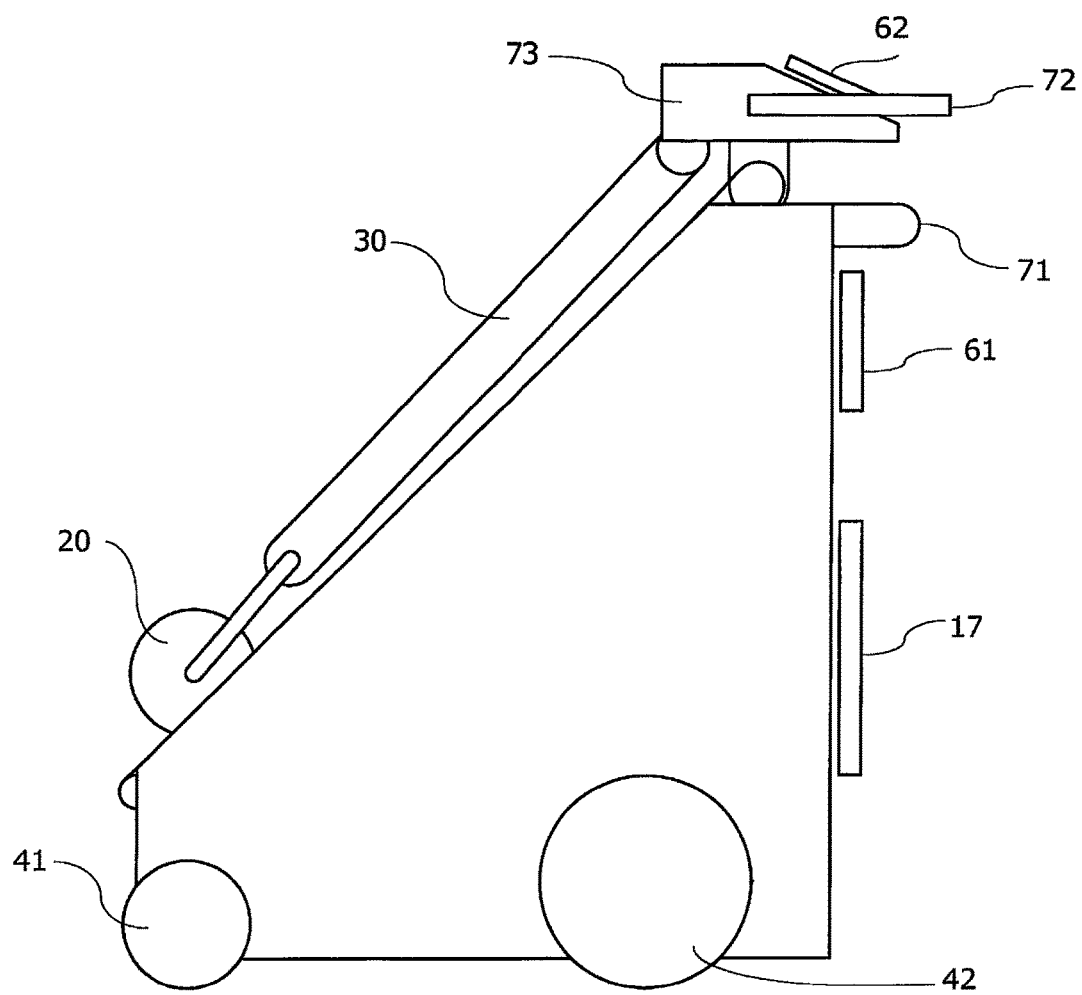
FIG. 2 is a side view of the mobile X-ray imaging device as shown in FIG. 1.
Figure 3:
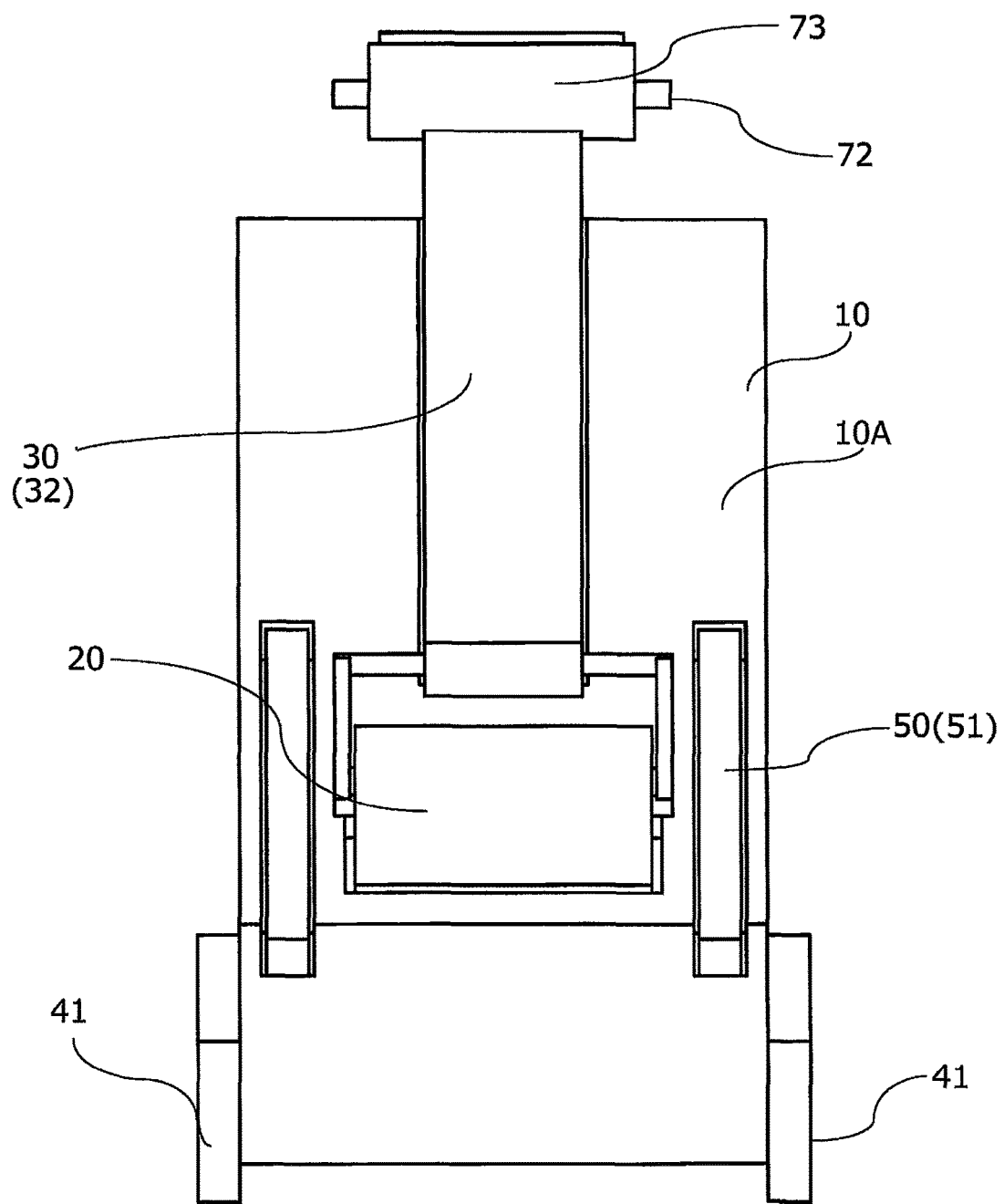
FIG. 3 is a front view of the mobile X-ray imaging device as shown in FIG. 1.
Figure 4:
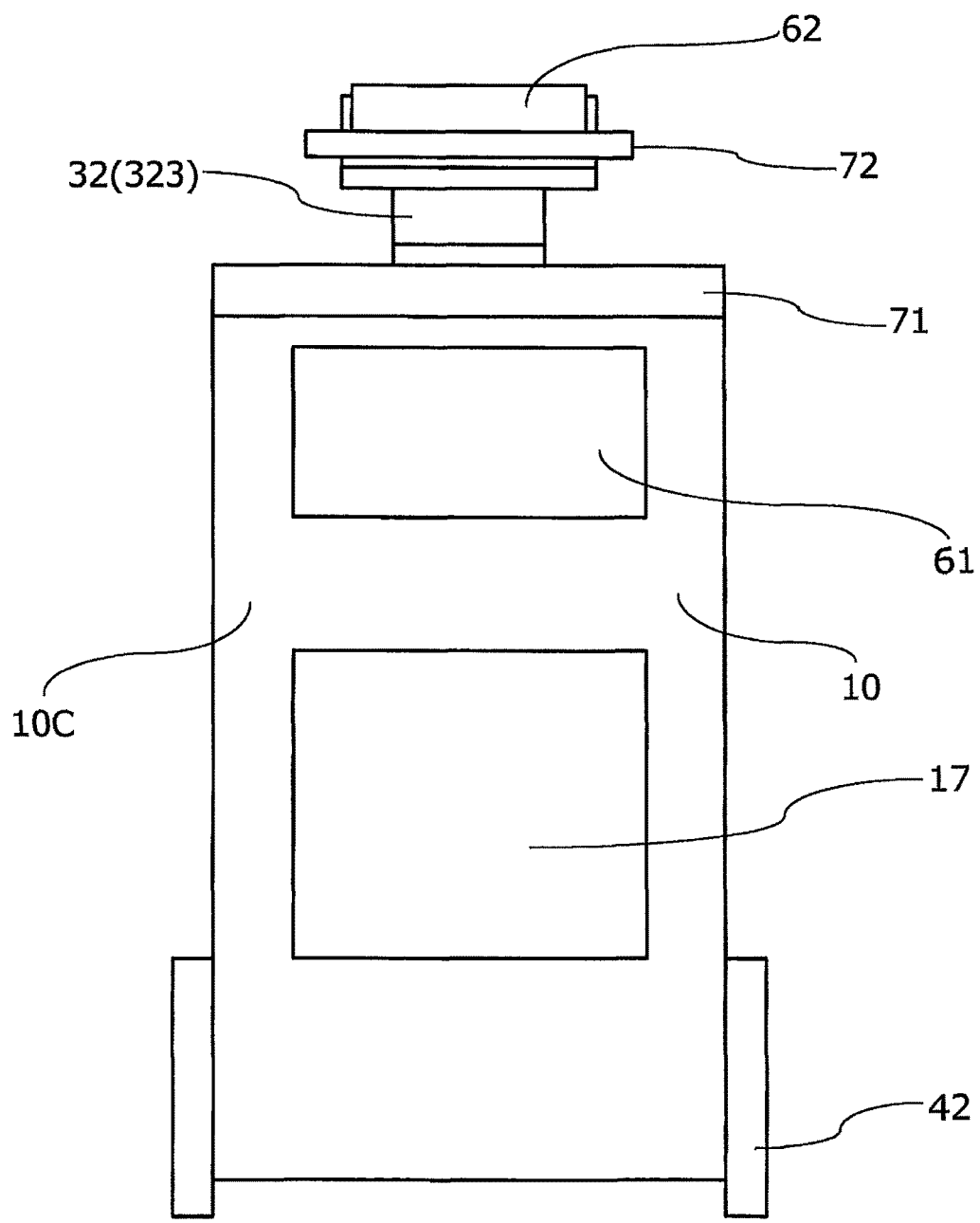
FIG. 4 is a rear view of the mobile X-ray imaging device as shown in FIG. 1.

With reference to FIGS. 1 to 4, an entire configuration of the mobile X-ray imaging device (hereinafter, simply referred to as "X-ray imaging device") according to the present embodiment will now be described. FIG. 1 is a perspective view of the X-ray imaging device viewed from the front; and FIGS. 2 to 4 are, respectively, a side view, a front view, and a rear view. In the present description, the left and right directions of FIG. 2 (side view) is referred to as the front and rear directions of the device, and the left and right directions of FIG. 3 is referred to as the left and right directions of the device.

As shown in FIGS. 1 and 2, the X-ray imaging device of the present embodiment comprises the main body 10 with the side surfaces of nearly triangle shape, the arm unit 30 fixed on the main body 10, the X-ray tube unit 20 fixed to one end of the arm unit 30, and the carriage (not illustrated). An enclosure constituting the main body 10 incorporates following elements, though not illustrated, such as a power supply unit for driving the carriage, a power supply unit or charging equipment for driving the X-ray tube unit 20, a control unit for driving the X-ray tube and controlling operations of mechanisms provided in the X-ray imaging device, and a balancer for controlling the center of gravity of the X-ray imaging device.

The bottom part of the main body 10 is mounted on the carriage (not illustrated) having wheels (front wheels 41 and rear wheels 42). The wheels may be mounted on the main body 10 (carriage) via a damper, a spring, or the like.

In the X-ray imaging device of the present embodiment, the front wheels 41 are casters to get the device to change direction, and the rear wheels 42 are driving wheels which are driven by the driving source, each with a diameter larger than the front wheel 41. It should be noted that the rear wheels 42 may be inclined with respect to a vertical plane, and in this case, the distance between the two rear wheels is the largest at a part coming into contact with a floor face. With this configuration, even in the case where the X-ray tube unit 20, being heavy and located forward of the rear wheels, is moved with respect to the main body 10, the main body 10 is brought into intimate contact with the floor face, thereby preventing unstable setup.

The rear wheel 42 being the driving wheel is provided with a lock such as an electronic lock for locking/unlocking the driving, allowing the device to travel only when it is unlocked.

The enclosure of the main body 10 comprises a front panel positioned on the front of the device, two side panels 10B of nearly triangle shape, and the back panel 10C positioned on the rear side. The front panel 10A connecting the two side panels 10B has an inclined plane with respect to a vertical plane, in association with the triangle shape of the side panels 10B.

On the front panel 10A, there is formed a storage concave 11 inwardly from the panel surface for storing a part or all of the arm unit 30. The arm unit 30 is pivoted on one end within this storage concave 11, and rotating around its pivot shaft (not illustrated) allows the arm unit to move from the state being stored in the storage concave 11 (FIG. 2) to the state being pulled out as shown in FIG. 1. The storage concave 11 is further provided with a slide mechanism for allowing one end of the arm unit 30 pivoted on the storage concave 11 to move along the longitudinal direction of the storage concave 11. With this slide mechanism, the arm unit 30 moves from the position at the bottom end of the storage concave 11 as shown in FIGS. 1 and 2, to the top end position. Details of the arm unit 30 and its support mechanism will be described in the following.

There is formed an X-ray tube storage 13 on the front panel 10A, continuing from the bottom end of the storage concave 11, for storing the X-ray tube unit that is fixed to the arm unit 30. As shown in FIG. 3, the X-ray tube unit 20 fixed to one end of the arm unit 30 is stored in the X-ray tube storage 13, in such a manner that an X-ray radiation window (aperture) of the X-ray tube unit 20 faces to the bottom of the X-ray tube storage 13, with the arm unit 30 being stored in the storage concave 11.

A support frame 50 is mounted on the front panel 10A for supporting a portable X-ray detector (not illustrated), and grooves for storing the support frame 50 are provided on both sides of the X-ray tube storage 13 and the storage concave 11. The X-ray detector may be publicly known, such as an FPD (Flat Panel Detector), and imaging is performed with positioning the X-ray detector 20 so that it is opposed to the X-ray tube unit 20, placing the subject therebetween. Accordingly, the position (posture) of the X-ray detector varies in relation to the X-ray tube unit 20, and the support frame 50 serves as a base for fixing one posture of the X-ray detector. Details of the support frame 50 will be described in the following.

On the other hand, as shown in FIG. 4, the back panel 10C of the main body 10 is provided with an X-ray detector storage 17 for storing the portable X-ray detector. Any structure is adaptable for use as the X-ray detector storage 17, as far as the X-ray detector can be supported stably, and any shape may be employed, such as a frame-like shape, and pocket-like shape.

The X-ray detector storage 17 may further be provided with a terminal for connecting the X-ray detector to the power supply unit and to an image forming unit, which are installed in the main body. In the case where the X-ray detector storage 17 is provided with this kind of terminal, for example, when the X-ray detector after imaging is completed is stored in the X-ray detector storage 17, the terminal of the X-ray detector is connected to the terminal of the storage 17, thereby allowing the X-ray detector to be charged, and enabling signals detected by the X-ray detector to be read by the image forming unit, so as to create and display an image. In addition, the X-ray detector storage 17 may also be provided with a source for emitting germicidal ultraviolet rays, or the like, and the source for emitting germicidal ultraviolet rays is configured to be activated when the X-ray detector is stored in the storage 17. With this configuration, the ultraviolet ray emission sterilizes the X-ray detector, every imaging time.

A display panel 61 for displaying GUI for prompting entry to the control unit and for displaying the image, and the like, as described above, is mounted on the upper part of the X-ray detector storage 17. An operation panel on which operating buttons are arranged may also be mounted, together with the display panel 61. The display panel 61 may be fixed on the main body 10, or detachable therefrom.

A transporting handle 71 (hereinafter, also simply referred to as a handle 71) for moving the X-ray imaging device is fixed on the top end of the back panel 10C. An operator stands behind the back of the X-ray imaging device, and pushes the transporting handle 71, allowing the X-ray imaging device to move to a desired place. The transporting handle 71 is provided with a dead man's switch (brake-release lever), though not illustrated. When the transporting handle 71 is gripped, this brake-release lever is pushed down, releasing the lock of the carriage (rear wheels 42), and while the lever is pushed down, the carriage is allowed to travel freely. When the push-down of the lever is canceled, the rear wheels 42 are locked.

The X-ray tube unit 20 comprises an X-ray tube and equipment/mechanisms attached thereto, and in the present embodiment, the X-ray tube unit incorporates an integrated X-ray generator where a cylindrical shaped X-ray tube and a high-voltage generator are accommodated in a single case, and a movable X-ray aperture fixed on the X-ray radiation window side. In addition, an infrared distance measurer for determining a position with respect to the X-ray detector, and the like, may be attached to the movable aperture. The high voltage generator may be connected to the power supply unit accommodated in the main body 10, via a cable not illustrated. The cable is led into the main body 10 through inside the arm unit 30.

As shown in FIG. 1, the X-ray tube unit 20 is fixed to the tip of the arm unit 30 via a holder 21 that is affixed to both ends of the cylindrical-shaped cover, enabling various movements such as bi-directional rotation and swing motion, whereby the X-ray emission side (aperture unit) can be oriented to any direction.

Figure 5:
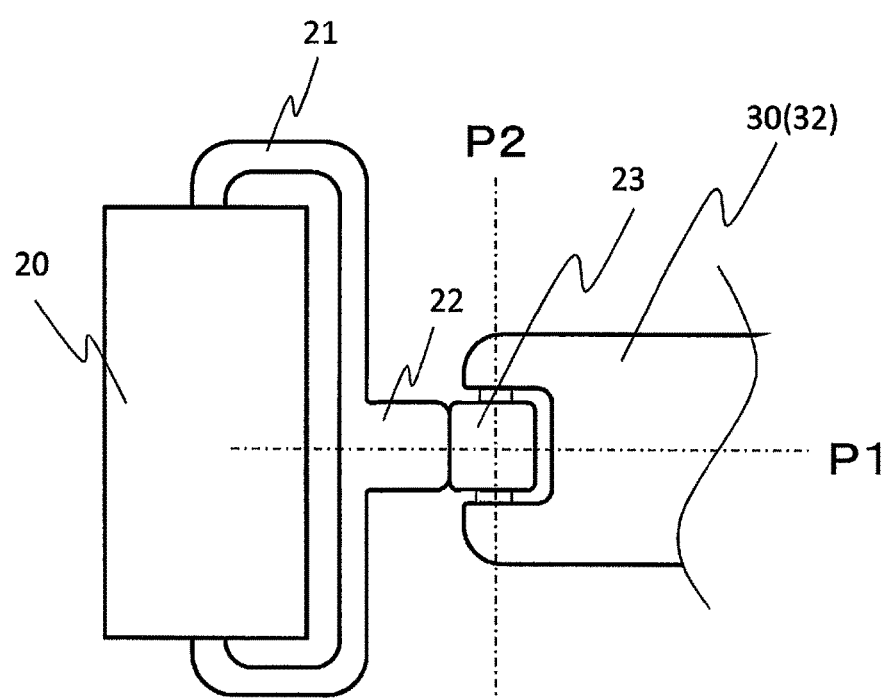
FIG. 5 illustrates a structure of the X-ray tube unit according to the first embodiment.

FIG. 5 illustrates one example of joint between the holder 21 of the X-ray tube unit 20 and the arm unit 30. In this example as shown in FIG. 5, the holder 21 has a first shaft 22 at the center thereof, and this first shaft 22 is pivoted on a second shaft 23 that is further pivoted on the tip of the arm unit 30. The first shaft 22 rotates about the axis P1 with respect to the second shaft 23, and the second shaft 23 rotates about the axis P2 orthogonal to the axis P1, with respect to the arm unit 30. With this configuration, by rotating the X-ray tube unit 20 about the axis P2, the X-ray radiation window varies its facing direction, downward, sideways (left or right), and further upward. In each of those states above, by rotating the X-ray tube unit 20 about the axis P1, the angle of the aperture unit can be changed. Further to those bidirectional rotations, it is possible to add rotation of the X-ray tube unit 20 with respect to the shaft 22, such as swing motion.

Rotations of the X-ray tube unit 20 about the axis P1 and about the axis P2 are limited to less than 360 degrees, so as to prevent wrenching the cable that is connected to the X-ray tube unit 20. It should be noted that the joint between the holder 21 of the X-ray tube unit 20 and the arm unit 30 is not limited to the structure as shown in FIG. 5, and as shown in FIG. 1, a structure that the shaft of the holder 21 is pivoted on the arm unit 30 may also be employed.

The aforementioned rotation and swing motion of the X-ray tube unit 20 may be based on manual operations or a power from a source such as a small-sized motor. A mechanical system or an electrical system may be employed as a mechanism for limiting the rotation angle. If the X-ray tube unit 20 is driven by electrical power, operation buttons may be provided on an arm operation handle described below, or the X-ray tube unit 20 may also be driven automatically by a controller. The X-ray tube unit 20 may be provided with a handle for manual operations (not illustrated).

Next, with reference to FIG. 6, details of the arm unit 30 will be described.

Figure 6:
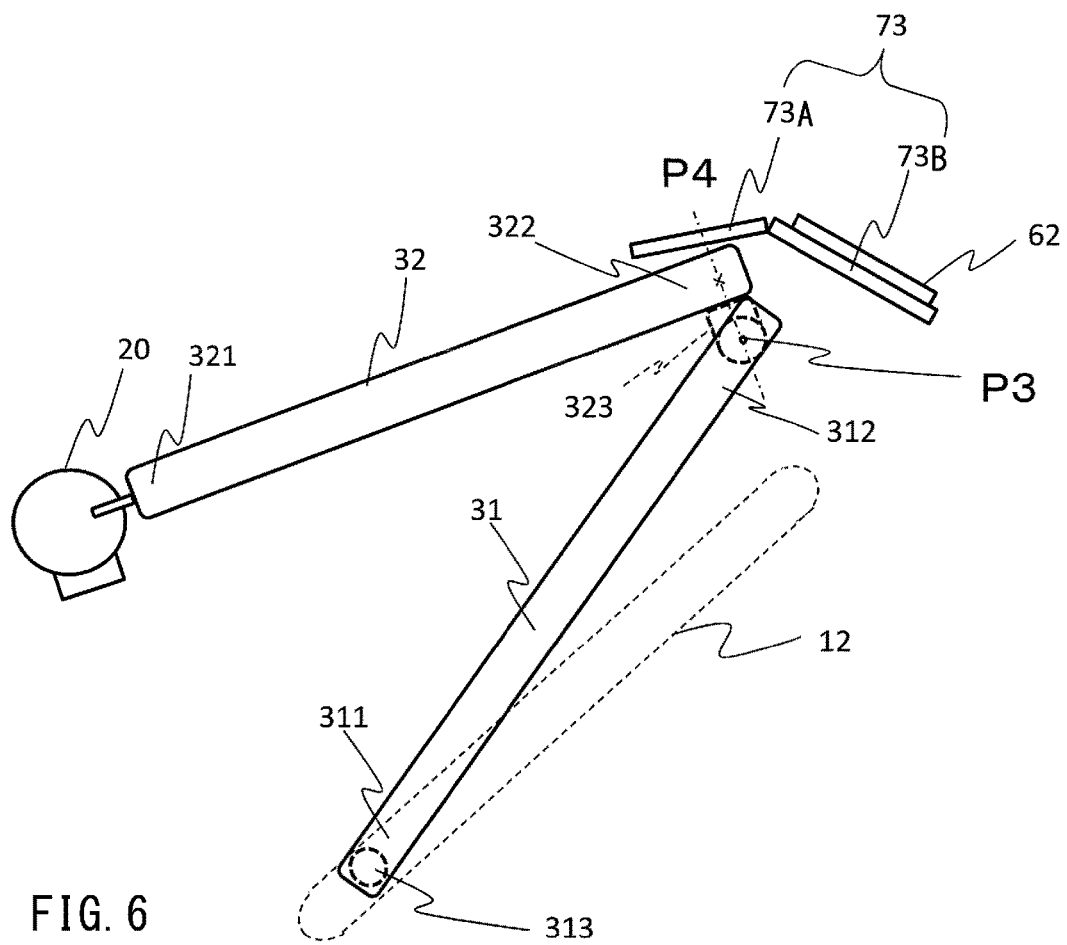
FIG. 6 illustrates a structure of an arm unit of the mobile X-ray imaging device according to the first embodiment.

As shown in FIGS. 1 and 6, the arm unit 30 in the present embodiment comprises two arms; a first arm 31 mounted on the main body 10 side and a second arm 32 to which the X-ray tube unit 20 is fixed, and the first arm 31 is foldably (rotatably) coupled to the main body 10, and the second arm 32 is coupled to the first arm 31 foldably (capable of opening and closing).

A rotation shaft of the first arm 31 is fixed on the end 311 thereof, being coupled to the main body 10, and the storage concave 11 of the main body 10 is provided with a slide mechanism for moving this rotation shaft in the longitudinal direction of the storage concave 11. A publicly known mechanism may be employed as the slide mechanism, and in the example here, long and narrow grooves or openings (guides) may be formed in the longitudinal direction, on the bottom of the storage concave 11 or on the sides thereof, and wheels 313 are provided on both sides of the rotation shaft fixed on the end 311 of the first arm 31. With this configuration, the wheels engage with the grooves, allowing a slide in the grooves. Any other combination may be applicable, in addition to the combination of groove and wheel, such as a combination of rail and wheel, and a combination of rack and pinion. Accordingly, the end 311 of the first arm 31 is allowed to move from the bottom end of the storage concave to the top end thereof.

The dotted line in FIG. 6 indicates, as the slide mechanism, the long and narrow openings (guides) 12 which are provided on the sides of the storage concave 11. The wheels 313 provided on the end of the first arm 31, engaging with the openings 12, are mounted on the shaft passing through the end 311 in the direction orthogonal to the longitudinal direction of the first arm 31. This configuration allows the first arm 31 to rotate about the shaft of the wheels, thereby varying the angle with respect to the front panel 10A.

The second arm 32 is fixed to the end 312 of the first arm 31, capable of opening and closing, as well as rotating, the end 312 being on the opposite side of the end 311 fixed on the main body 10. As shown in FIG. 6, for instance, the end 322 of the second arm 32 is coupled to the end 312 of the first arm 31, via the shaft 323. The shaft 323 is pivoted on the axis P3 at the end 312 of the first arm 31, allowing rotation about the axis P3. The end 322 of the second arm 32 is pivoted on the axis P4 with respect to the shaft 323, allowing rotation (swiveling) around the axis P4.

It should be noted that the mechanism as shown in FIG. 6 is an example for achieving the foregoing movement of the second arm 32 with respect to the first arm 31. On the contrary, it may be configured such that the shaft 323 rotates about the axis P4 with respect to the first arm, and the second arm 32 rotates about the axis P3 with respect to the shaft 323. Further alternatively, another joint mechanism may be employed.

The aforementioned sliding and rotation (variation of the opening angle) of the first arm 31, and the rotation about the axes P3 and P4 (variation of the opening angle and the swiveling angle) of the second arm 32, may be performed manually by using the arm operating handle described in the following. Alternatively, an electrical drive source such as a motor (not illustrated) may be utilized subsidiarily. The driving source may facilitate moving of the arm unit 30 on which the weighty X-ray tube unit 20 is mounted, with the use of the handle or operation equipment, and further, operation of the arm unit 30 may be semi-automated.

The arm unit 30 is further provided with a mechanism (not illustrated) for locking and unlocking the first and second arms 31 and 32 at a predetermined slide position or rotational position, in association with the slide mechanism and the rotation mechanism of the first arm 31, and the rotation mechanism of the second arm 32. The lock mechanism functions as locking the sliding and rotation of the first and second arms 31 and 32, mechanically or electrically, and an electromagnetic lock may be employed, for instance. Locking and unlocking can be performed by operating a pedal, lever, or button.

Preferably, the arm unit 30 may further be provided with a position detector such as encoder, for detecting a position in the slide direction, the opening angle, and swiveling angle of the first and second arms 31 and 32. When the arm unit 30 is moved by using the drive source, detected results of the positions and angles of the first and second arms 31 and 32, obtained by the position detector may be utilized for controlling the arm unit 30.

Next, an arm operating handle 72 (hereinafter, it is also simply referred to as a handle 72) for operating the arm unit 30 by the operator will be described. The arm operating handle 72 is provided on the joint between the first arm 31 and the second arm 32. As shown in FIG. 1, in the present embodiment, a cover 73 is provided for covering the joint, and the handle 72 is fixed on this cover 73.

Figure 7:
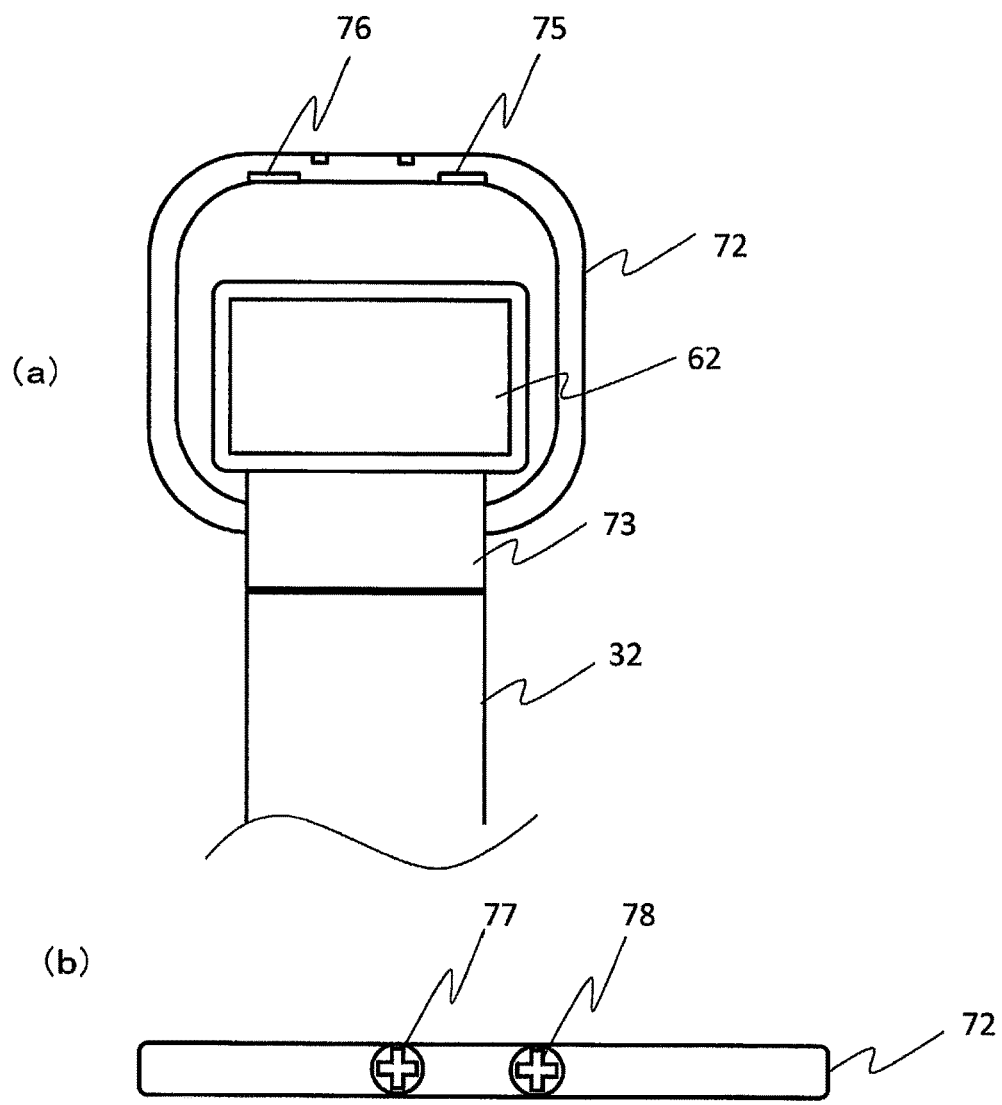
FIG. 7 illustrates a handle of the mobile X-ray imaging device of the first embodiment.

As shown in FIG. 7(a), in the present embodiment, the handle 72 is provided with the dead man's switches 75 and 76, which keep movement while those switches are pressed down. Press-down of the switches 75 and 76 according to an action of grasping the handle 72 may release the lock mechanism, e.g., an electromagnetic lock for locking the positions of the first arm and the second arm, thereby enabling movement of the arms. As for the slide position, the lock may be released only when both the switches 75 and 76 are pressed down, for instance. Alternatively, a switch for locking/unlocking the slide position may be provided, in addition to the switches 75 and 76.

With this configuration, by lifting up the handle 72, for instance, the end 312 of the first arm 31 is raised, thereby varying the angle (opening angle) with respect to the main body 10. By raising the handle 72 backwardly and upwardly from the device, the end 311 of the first arm 31 is made to slide to move toward an upper part of the storage concave 11. This sliding toward the upper part of the first arm 31 may be associated with the opening angle. In this case, along with upward sliding of the first arm 31, the opening angle is made larger, configuring such that the first arm 31 becomes nearly upright when the first arm 31 is moved to the top end of the storage concave 11.

After raising the first arm 31 up to a predetermined slide position, the slide mechanism is locked, and then the opening angle between the first arm 31 and the second arm 32 is adjusted.

If the switches 75 and 76 are not operated, both the first arm 31 and the second arm 32 are locked and immovable. However, if the switch 76 is pressed down, for example, while the handle 72 is being grasped, the lock of the second arm 32 is released. In this situation, when the operator presses down or presses up the handle 72, the second arm 32 rotates about the axis P3, resulting in that the end 321 to which the X-ray tube unit 20 is fixed goes up or down, thereby varying the position of the X-ray tube unit 20. By suspending the press-down operation of the switch 76, the second arm 32 is retained at the position.

Turning the handle 72 left and right, in the state that rotation of the first arm 31 and the second arm 32 in the opening-angle direction is locked, enables the second arm 32 to revolve, i.e., to swivel around the axis P4. Accordingly, the X-ray tube unit 20 is allowed to swivel laterally.

Manipulation of the arm unit 30 as described above is just an example, and it does not restrict the present embodiment. In the case where the sliding and rotation of the first arm 31, and the rotation of the second arm are performed by electrical drive units, the aforementioned lifting operation, raising operation, or turning operation according to the operating handle 72 may trigger transmission of control signals to activate the drive unit.

As shown in FIG. 7(b), the handle 72 may be provided with operation buttons 77 and 78 for rotating the X-ray tube unit 20. In the illustrated example, the operation buttons 77 and 78 are provided for the rotation of the X-ray tube unit 20 as shown in FIG. 5, respectively about the axis P1 and about the axis P2, and those buttons are provided on the positions facilitating manipulation by the thumb of a hand grasping the handle 72, for example, on the outside surface of the handle 72. With this configuration, the X-ray tube unit 20 can be manipulated to rotate and swing, even from a location away from the X-ray tube unit 20, so as to set the X-ray tube unit 20 at a position facing the X-ray detector.

The cover 73 that covers the joint between the first arm 31 and the second arm 32 is fixed (pivoted) on the end 322 of the second arm 32, and the ends of the handle 72 described above are integrally fixed to the sides of the cover. The shape of the cover 73 is not particularly limited, but in the embodiment as illustrated, two top panels 73A and 73B (FIG. 6) are coupled to each other at an obtuse angle, having a shape of a plate joining slim side-panels to both sides of the plate. In FIG. 6, the side-panels are not shown, and only the top panels 73A and 73B are schematically illustrated.

Even when the first arm 31 rotates, the cover 73 allows the upper plate 73A to keep a nearly horizontal position.

Out of the top panels 73A and 73B constituting the cover 73, a second display panel 62 is provided on the top panel 73B that is positioned on the handle 72 side, in addition to the display panel 61 (the first display panel). The second display panel 62 may be provided with a display function which is different from the display panel 61 fixed on the back side of the main body 10, or it may be provided with a display function that supplements the display panel 61. By way of example, the display panel 62 may be dedicated to GUI for operation, or a display panel for displaying an image, or it may be function as a display for both purposes. The display panel 62 may be fixed on the cover 73, or it may be detachable from and attachable to the cover 73. As described above, since the cover 73 is made up of the top panels 73A and 73B being joined at an angle, a tilt angle of the display panel 62 is given with respect to the horizontal plane, facilitating viewing of the screen by the operator.

Figure 8:
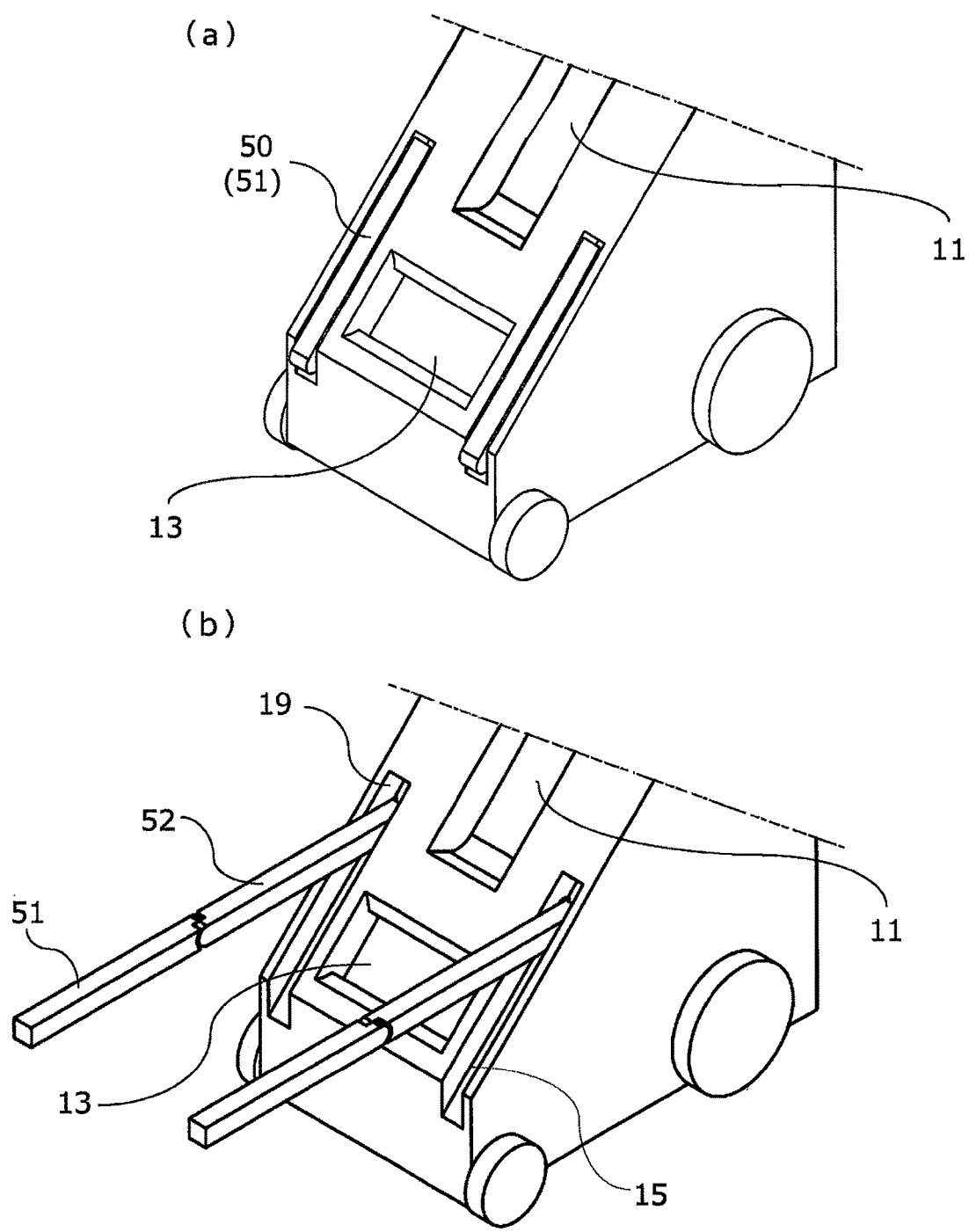
FIG. 8 illustrates a support frame of the X-ray detector of the mobile X-ray imaging device as shown in FIG. 1.

Next, with reference to FIG. 8, a structure of the support frame 50 of the X-ray detector will be described. As shown in FIG. 8(*b*), the support frame 50 is made up of a pair of parallel rod like members, and each rod like member has a structure joining two members (a supporting member 51 and a link member 52). The link members 52 are inserted into the main body via two openings 19 provided on the main body 10, and the link members are supported by a supporter, not illustrated, inside the main body 10, in a manner movable upwardly and downwardly, and also rotatably.

In the embodiment being illustrated, the openings 19 are formed in a long and narrow shape along both sides of the X-ray tube storage 13 on the front panel 10A, and there are formed grooves 15 for storing the support frame 50, on the lower side of the front panel 10A, continuously from the openings 19, respectively. The grooves 15 are vertical two grooves, being parallel to each other.

As shown in FIG. 8(*a*), in the aforementioned configuration, when the support frame 50 (rod-like members) is folded and stored in the grooves 15, the support frame 50 can be put within mostly the same plane as the panel surface of the front panel 10A. Since the support frame 50 is made up of two rod-like members, when the arm unit 30 is folded so as to store the arm unit 30 and the X-ray tube unit 20 respectively in the storage concave 11 and the storage 13, both the arm unit 30 and the X-ray tube unit 20 can be received from upside in the respective storage, without bumping the X-ray tube unit 20 against the support frame 50, in the state where the support frame 50 are stored in the front panel 10A.

The height of the support frame 50 can be adjusted by moving the link members 52 up and down along the openings 19. With this configuration, a distance can be adjusted between the X-ray detector set on the supporting members 51, and the X-ray tube unit 20 placed in a manner opposed to the X-ray detector, putting a subject therebetween. If the X-ray tube unit 20 is provided with a distance measurer, the distance between the X-ray detector and the X-ray tube unit 20 is adjusted by using this distance measurer.

FIG. 8 illustrates the support frame 50 made up of rod-like members. The shape of the support frame 50 is not limited to the rod-like shape and may be changed to any shape, such as H-shape, as far as there is no interference with movements of the arm unit 30 and the X-ray tube unit 20.

Figure 9:
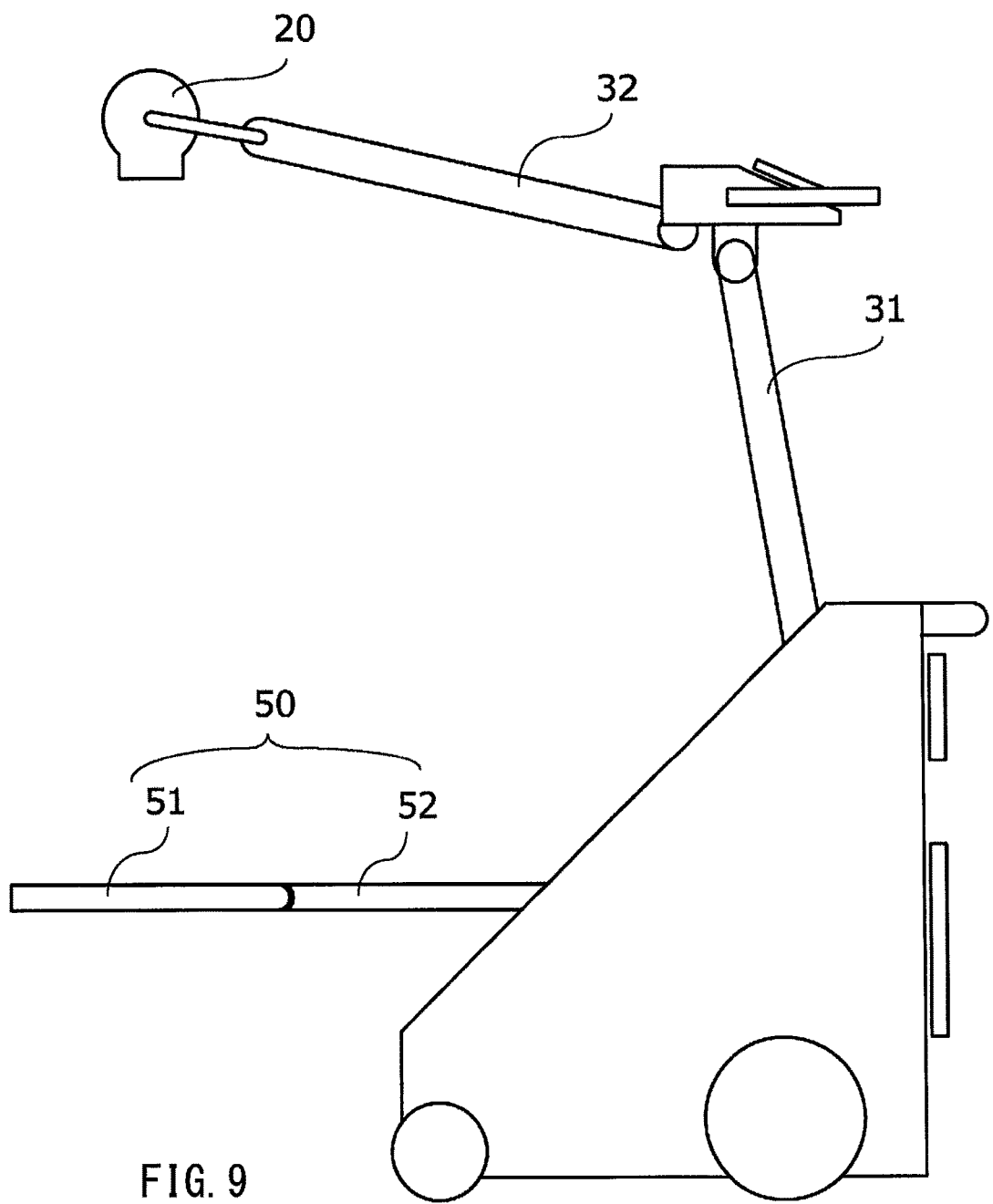
FIG. 9 is a side view showing one posture example of the mobile X-ray imaging device as shown in FIG. 1.
Figure 10:
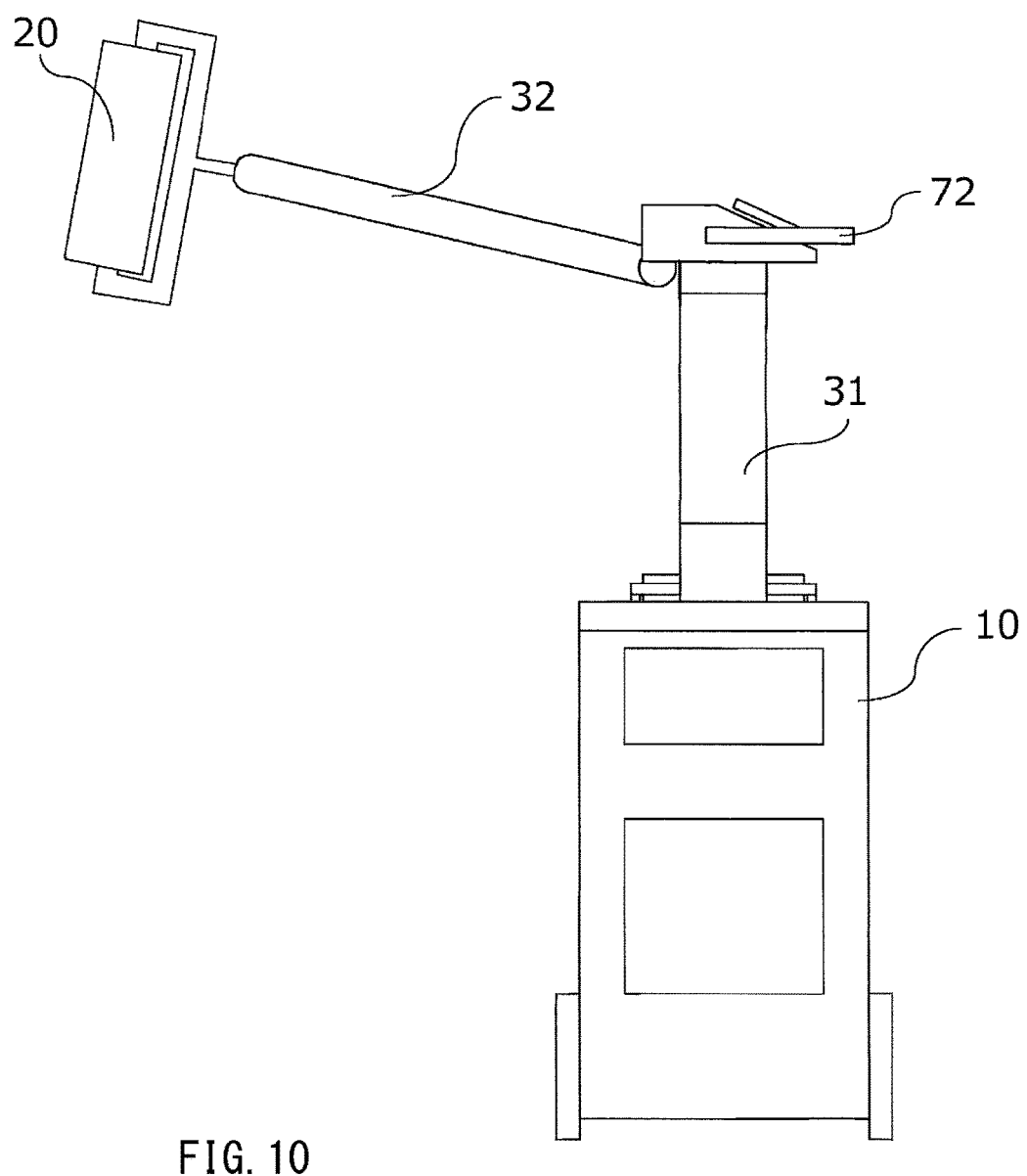
FIG. 10 is a rear view showing another posture example of the mobile X-ray imaging device as shown in FIG. 1.

According to the movements of the arm unit and the support frame as discussed so far, various imaging postures can be achieved. FIG. 9 and FIG. 10 illustrate examples thereof.

FIG. 9 illustrates that the first arm 31 is moved to the top end in the slide direction, maximizing the opening angle, and the second arm 32 is opened so that the longitudinal direction becomes nearly horizontal. In this state, when the support frame 50 is pulled out and the X-ray detector is put on the supporting member 51, the X-ray tube unit 20 is positioned substantially opposed to the X-ray detector. The subject is placed in any posture between the X-ray tube unit 20 and the X-ray detector, and the position of the X-ray tube unit is adjusted so that the position irradiated with X-rays coincides with the X-ray detector, and this allows imaging.

In FIG. 10, the second arm 32 is swiveled by approximately 90 degrees with respect to the first arm 31 from the state of FIG. 9, and further, the X-ray tube unit 20 is rotated so that X-ray radiation window faces sideways. In this posture, for example, imaging can be performed with making the subject stand up or sit on a chair, in a manner facing the X-ray tube unit 20. The height of the X-ray tube unit 20 can be adjusted by changing the slide position and the opening angle of the first arm 31, the opening angle of the second arm 32, or the like.

The X-ray imaging device of the present embodiment has been described, mainly focusing on the structure and the shape thereof. Major effects that are yielded by those structure and shape will be exemplified.

The X-ray imaging device of the present embodiment has the structure that the X-ray tube is supported by the foldable arm unit, not by a strut, and the arm unit can be stored in the front panel of the main body enclosure, whereby it is possible to shift the location of the X-ray imaging device, without interrupting sightlines of an operator who manipulates the device with standing at the back of the main body. In particular, the front panel is an inclined plane which slopes from the back toward the front, and thus the field of vision opens up to the front of the device, thereby preventing the device front end from bumping against an object or a person. If the shape of the inclined plane is made as a curved surface being convex upwardly, it is possible enlarge the storage volume of the main body enclosure, with ensuring the view from the back toward the front.

In addition to the foregoing features, the X-ray imaging device of the present embodiment is provided with a mechanism that the end of the arm unit coupled to the main body enclosure slides in the storage concave, thereby enlarging the movable range of the arm unit. Accordingly, even in a limited space for installing the device, such as a patient room, this allows imaging with various postures, through extension and contraction of the arm unit from various heights to a desired position.

In addition, the X-ray imaging device of the present embodiment is provided with the storage for storing the X-ray tube, continuing from the storage concave for storing the arm unit, whereby the X-ray tube can be protected when moving the device or when the device is put back in place.

The X-ray imaging device of the present embodiment is further provided with the handle on the joint between two arms constituting the arm unit, enabling movement of the X-ray tube via the arm unit, without forcing the operator to take an unnatural posture, even when the X-ray tube unit is at a high position. By way of example, conventionally, it has been hard for the operator who is short in height to manipulate the X-ray tube at a high position, but this problem is now solved. On the contrary, when the X-ray tube is at a low position, it is also possible to lift up and rotate the X-ray tube by handle, in a standing posture.

The arm operating handle is further provided with switches for manipulating rotation of the X-ray tube with respect to the arm unit, thereby enhancing operability.

The X-ray imaging device of the present embodiment is further equipped with the supporting frame for placing the X-detector on the front panel, and this allows imaging with the X-ray detector that is placed stably on a definitive place by utilizing the supporting frame. The supporting frame is installed on the main body, in a movable manner vertically, whereby the X-ray detector can move up and down in a manner adaptive to the height of the subject, and also a distance from the X-ray tube unit can be adjusted.

In addition, the grooves for storing the supporting frame that is folded into the front panel are provided on both sides of the storing concave/X-ray tube storage. Accordingly, when the device is moved or put back in a place, there is no protrusion from the front panel, preventing breakage of the supporting frame due to a contact with an object or a person.

Modification Example 1 of the First Embodiment

It is described in the first embodiment that the end 311 of the first arm 31 as the joint with the main body is positioned at the bottom end of the storage concave 11 in the state that the arm unit 30 is folded and stored in the storage concave 11. Alternatively, it is possible to couple the arm unit 30 with the main body, in such a manner that the end 311 of the first arm 31 is positioned at the top end of the storage concave 11 when the arm unit 30 is folded.

In this case, the X-ray tube unit 20 is positioned on the upper side of the storage concave 11 in the state where the arm unit 30 is folded and stored, and therefore, it is preferable to provide the storage 13 for storing the X-ray tube unit 2 continuously from the upper side of the storage concave 11.

The structure and movement of the arm unit 30 are similar to the first embodiment in this modification example. In this modification example, the X-ray tube unit 20 is located on the upper part of the device when the device is moved, i.e., when the arm unit is stored, and thus, it is possible to avoid collision of the X-ray tube unit with an object or a person with higher reliability. In this case, however, an aperture unit of the X-ray tube unit assumes a posture facing upward, and therefore it is preferable to provide a protective cover.

Modification Example 2 of the First Embodiment

It is described in the first embodiment that the arms constituting the arm unit are made up of members each having a fixed length. However, a mechanism capable of expansion and contraction may be added to the arm.

Figure 11:
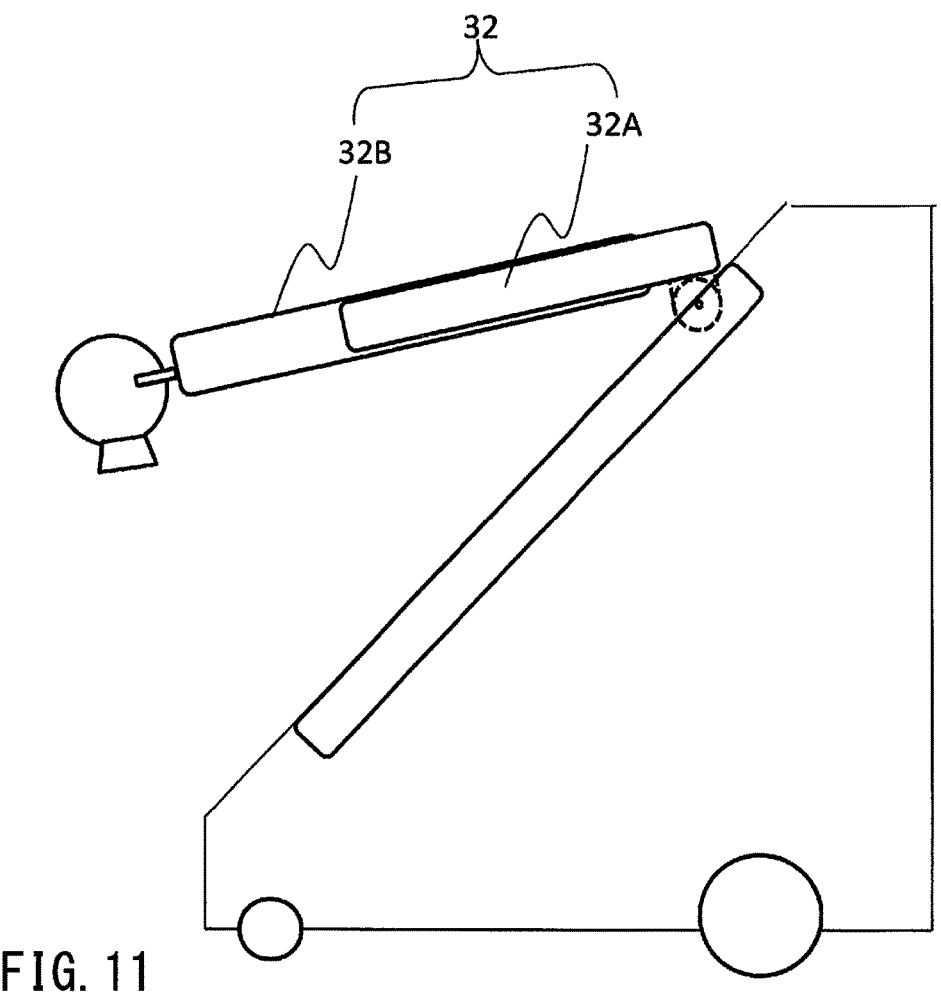
FIG. 11 illustrates modification example 1 of the mobile X-ray imaging device according to the first embodiment.

FIG. 11 illustrates that the mechanism capable of expansion and contraction is added to the second arm. As illustrated, the second arm 32 is made up of an outside arm 32B to which the X-ray tube unit 20 is fixed, and an inside arm 32A that is coupled to the first arm 31. The outside arm 32B has inner space for accepting the inside arm 32A. The inside arm 32A fits into this space, and it is inserted slidably therein along the longitudinal direction. The end of the inside arm inserted in the outside arm and the end of the outside arm are structured to be engaged with each other, so that the inside arm 32A does not detach from the outside arm 32B. By way of example, the inside arm 32A can be driven by a drive unit, e.g., a hydraulic cylinder provided inside the outside arm 32B, and it is slidable within the outside arm 32B.

In this modification example 2, the expansion and contraction mechanism is provided to the arms, thereby enlarging the movable range of the X-ray tube unit 20, the range being restricted by the length of the arm, without extending the length of the arm unit 30 in the folded state. In other words, it is possible to perform imaging at a distance from the main body, with ensuring a wide view toward the front in shifting the X-ray imaging device.

Modification Example 3 of the First Embodiment

It is described in the first embodiment that the arm unit is made up of two arms, but the number of arms is not limited to two.

Figure 12:
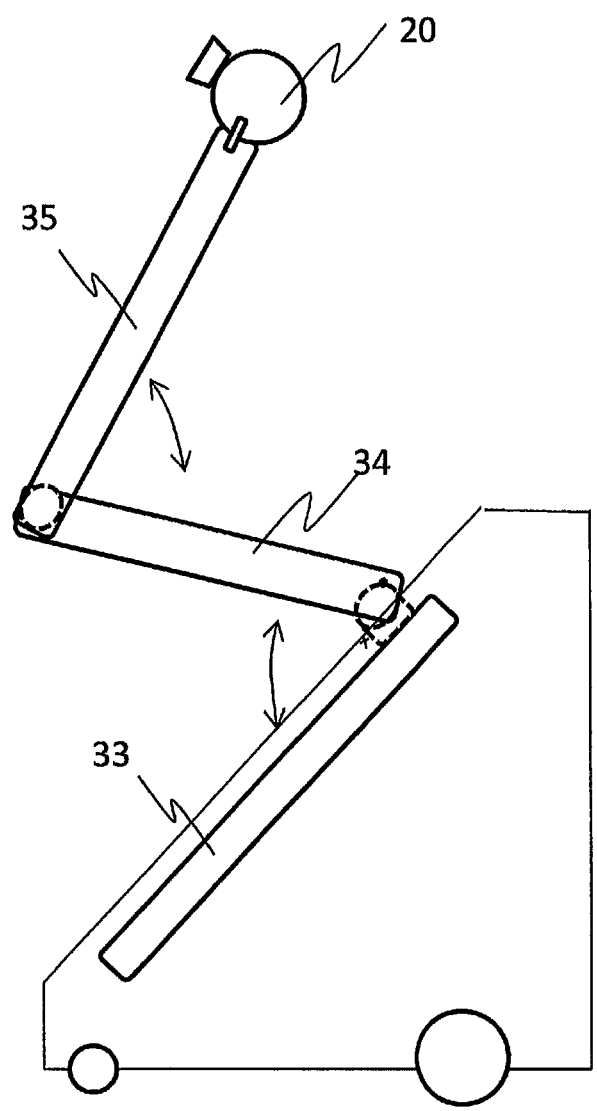
FIG. 12 illustrates modification example 2 of the mobile X-ray imaging device according to the first embodiment.

FIG. 12 illustrates an example that three arms constitute the arm unit. As illustrated, the arm unit is made up of the first arm 33, the second arm 34, and the third arm 35. The end of the first arm 33 is slidably installed to the storage concave that is formed on the main body 10, and the X-ray tube unit is fixed to the end of the third arm 35.

The end of the first arm 33 and the end of the second arm 34 are coupled with each other enabling rotation of two directions orthogonal to each other, similar to the coupling between the first arm and the second arm according to the first embodiment.

In the state where the angles formed by the folded arms at respective joints are minimized, the three arms 33 to 35 of the arm unit of the X-ray imaging device according to the present modification example, become almost parallel to one another, and a part or all of the arm unit is stored in the storage concave that is provided on the front panel of the main body. By changing the angles formed by the arms 33 to 35 and arm swiveling angles thereof appropriately, the postures as shown in FIGS. 9 and 10 can be taken in addition to the posture as shown in FIG. 12, whereby the X-ray tube can be positioned at any point.

In the X-ray imaging device of the present modification example, the X-ray tube unit is positioned above the storage concave in the state that the arm unit is stored in the storage concave. Therefore, it is possible to avoid collision of the X-ray tube unit with an object or a person with higher reliability.

Second Embodiment

In the first embodiment, a structure of the X-ray imaging device has been described mainly. The present embodiment features that a control unit of the X-ray imaging device has functions to control the mechanisms that constitute the X-ray imaging device.

In other words, the mobile X-ray imaging device of the present embodiment is further provided with the control unit for controlling movement of the arm unit. The mobile X-ray imaging device of the present embodiment is further provided with a detector for detecting a position of the X-ray tube, and the control unit controls the movement of the arm unit on the basis of the detected position of the X-ray tube.

Individual mechanisms in the mobile X-ray imaging device according to the first embodiment are provided with a limited movable range. Moving the X-ray tube unit 20 with the use of a combination of plural movable ranges may cause an inappropriate positioning of the X-ray tube unit 20, depending on the way of combination, though each mechanism moves or rotates within each movable range. By way of example, such inappropriate positioning includes a possibility that the X-ray rube unit may take a position interfering with the main body enclosure, or a position that upsets the balance of the device. In the present embodiment, the control unit controls the mechanisms so that the X-ray tube unit 20 may not exceed a predetermined movable range, regulating the X-ray tube unit 20 so as not to move to the inappropriate position as described above.

The structure of the X-ray imaging device of the present embodiment is similar to that of the other embodiment as described above, and redundant descriptions will not be made. Hereinafter, a description will be made focusing on functions of the control unit. In this description, the figures and labels used in describing the first embodiment will be referred to as appropriate.

Figure 13:
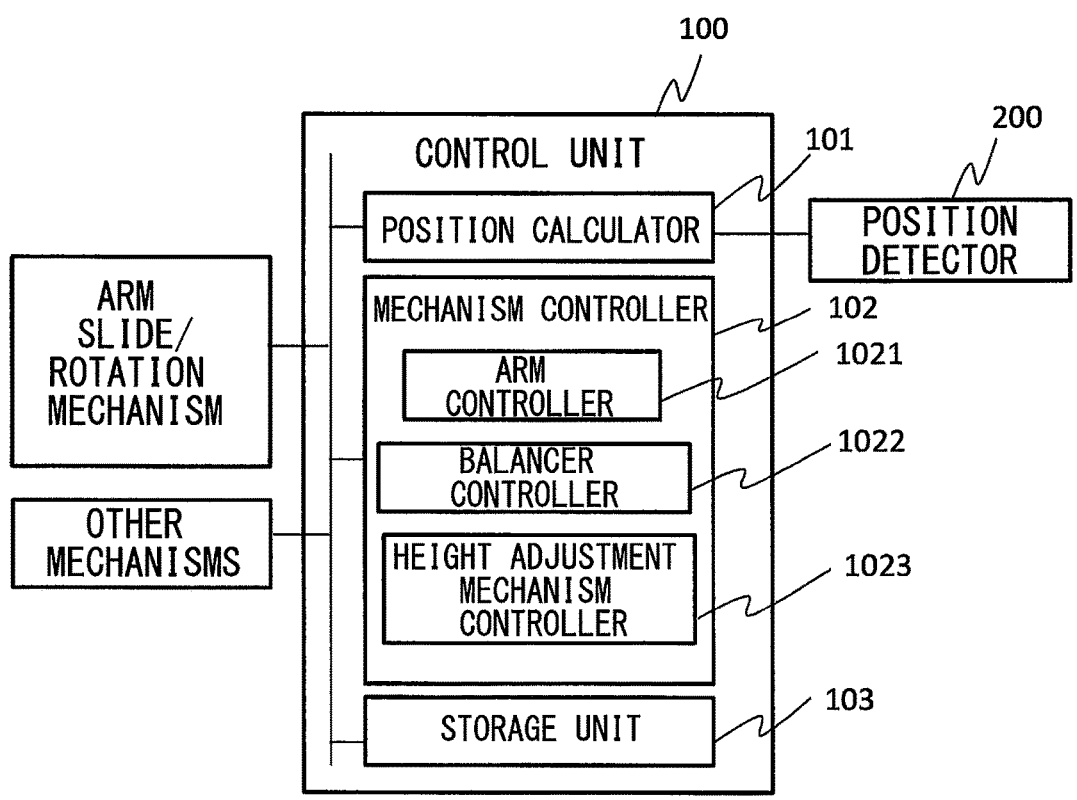
FIG. 13 is a functional block diagram of a controller of the mobile X-ray imaging device according to a second embodiment.

FIG. 13 illustrates a functional block diagram of the control unit. The control unit 100 is provided with, as primary functions, a position calculator 101 for calculating a position of the X-ray tube unit 20, a mechanism controller 102 for controlling mechanisms on the basis of positional information of the X-ray tube unit 20, calculated by the position calculator 101, and a storage unit 103 for storing data, and the like, necessary for controlling. In addition to the functions as shown in FIG. 13, the control unit also controls starting and completion of imaging, including X-ray radiation from the X-ray tube. However, controls regarding the imaging operation will not be described here.

Elements incorporated in the mechanism controller 102 are respectively associated with the mechanisms provided in the X-ray imaging device. FIG. 13 shows an arm controller 1021, a balancer controller 1022, and a height adjustment mechanism controller 1023, and a part of those elements may be omitted or other element may be added depending on the device structure. In the present embodiment, the device provided with the arm controller 1021 will be described.

The mechanism of the arms controlled by the arm controller 1021 includes, a mechanism for sliding the first arm, a mechanism for rotation, a mechanism for rotating the second arm, a mechanism for swiveling, and the like. If a mechanism for expanding and contracting the arm is added, the expansion and contraction mechanism may also be included. The arm controller 1021 also controls mechanisms of the X-ray tube unit, including a mechanism for rotating the X-ray tube in two directions (two rotation mechanisms) and a mechanism for swinging.

The position calculator 101 obtains positional information of the X-ray tube unit 20 from the position detector 200. The position detector 200 may be a detector for directly detecting the position of the X-ray tube unit 20 by using infrared radiation or magnetism, or it may be a detector for detecting a slide position of the slide mechanism or a rotation angle of the rotation mechanism of the arm unit 30. Data including the rotation angle can be obtained by providing a sensor (position detector) such as an encoder in each rotation mechanism, for sensing a rotation amount. If a drive source for electrically driving the rotation is provided, data of the rotation amount can be obtained based on a drive volume of the drive source.

Figure 14:
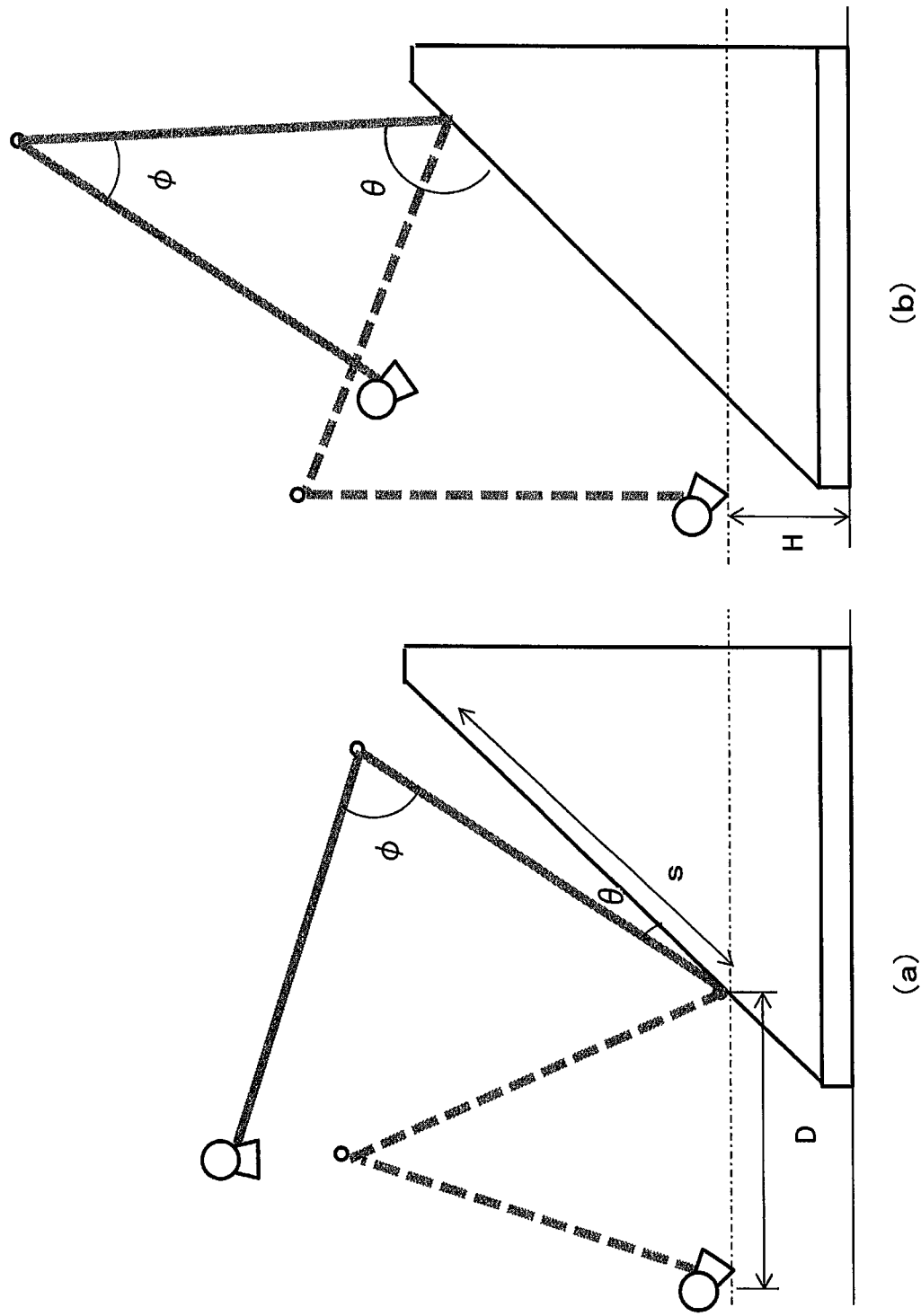
FIGS. 14(a) and (b) illustrate a movable range of the arm unit according to the second embodiment.

By way of example, the positional information of the X-ray tube unit 20 is obtained from the rotation angles, and the like, respectively of the arms 31 and 32 constituting the arm unit of the X-ray tube unit 20. In other words, the lengths of the first arm 31 and the second arm 32, and the distance from the end 321 of the second arm 32 to the X-ray tube unit 20 are constant. Therefore, as shown in FIGS. 14 and 15, the position of the end 312 of the first arm 31 can be specified from the position (s) in the slide direction, and the rotation angle ($\theta$) of the first arm 31, and the positions of the end 321 of the second arm 32 and the X-ray tube unit 20 can be specified from the rotation angle ($\varphi$) and swiveling angle ($\psi$) of the second arm 32.

Figure 15:
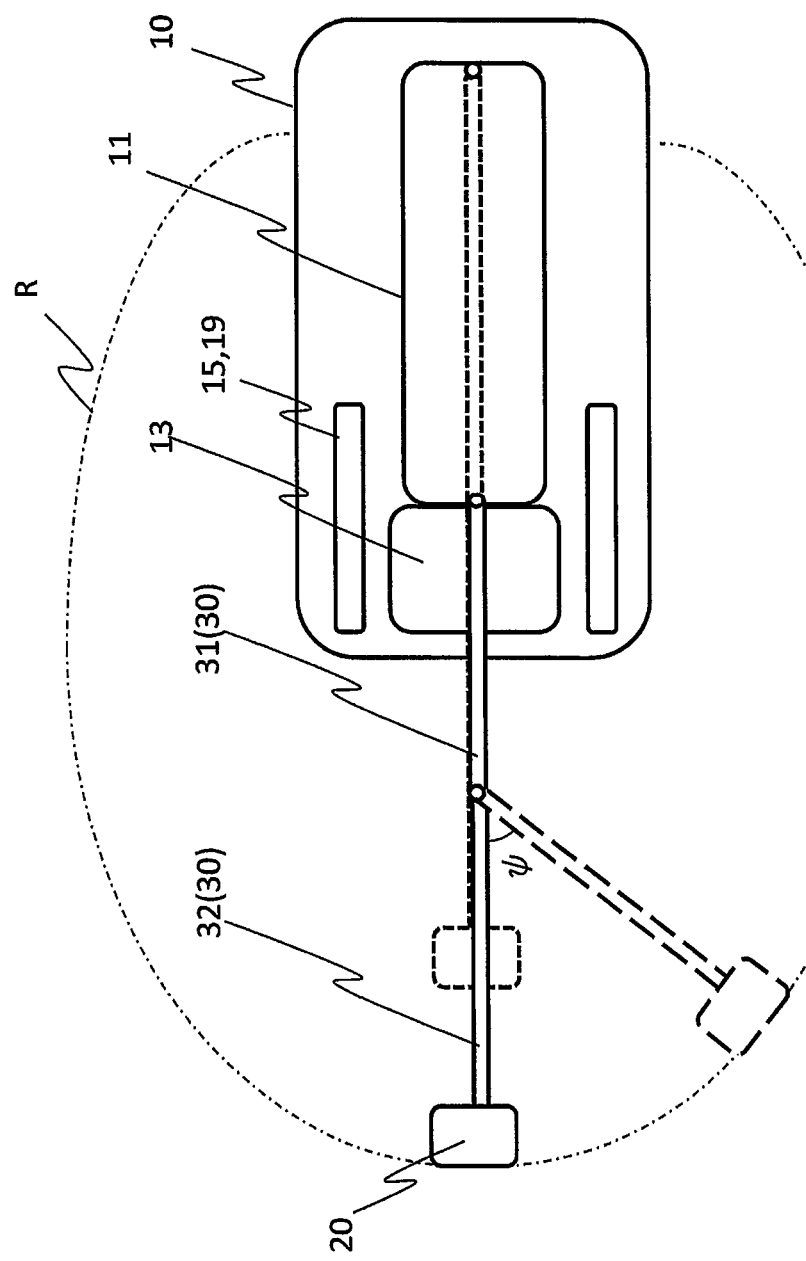
FIG. 15 illustrates the movable range of the arm unit according to the second embodiment.

The storage unit 103 stores movable range R (inner range surrounded by the dotted line) as shown in FIG. 15, for instance, in the form of position coordinate assuming a predetermined point of the device as the origin of the coordinate. FIG. 15 illustrates the movable range R in a plan view, however, actually, the movable range has a limitation also in the height direction. That is, the movable range may be a three-dimensional range, such as a cylindrical shape with a predetermined height having the oval-shaped cross section, as shown in FIG. 15, and a body of rotation formed by rotating a nearly oval shape around the axis in the longitudinal direction. In addition, in order to avoid collision of the X-ray tube unit 20 with the main body 10, the range of the main body 10 is excluded from the movable range R.

Instead of predetermining the movable range of the X-ray tube unit 20, it is also possible to determine movable angle ranges respectively of the first arm and the second arm, at every position in the slide direction of the first arm 31, and store those movable angle ranges.

The mechanism controller 102 (the arm controller 1021) transmits signals to the mechanisms for driving the arm unit 30, on the basis of the position of the X-ray tube unit 20 and the positional information of each of the arms 31 and 32, calculated by the position calculator 101, and controls motions of the mechanisms so that the X-ray tube unit 20 is moved without exceeding the ranges stored in the storage unit 103. Alternatively, a lock element of the mechanisms is actuated, for locking the mechanism so as to avoid movement that exceeds the movable range.

Figure 16:
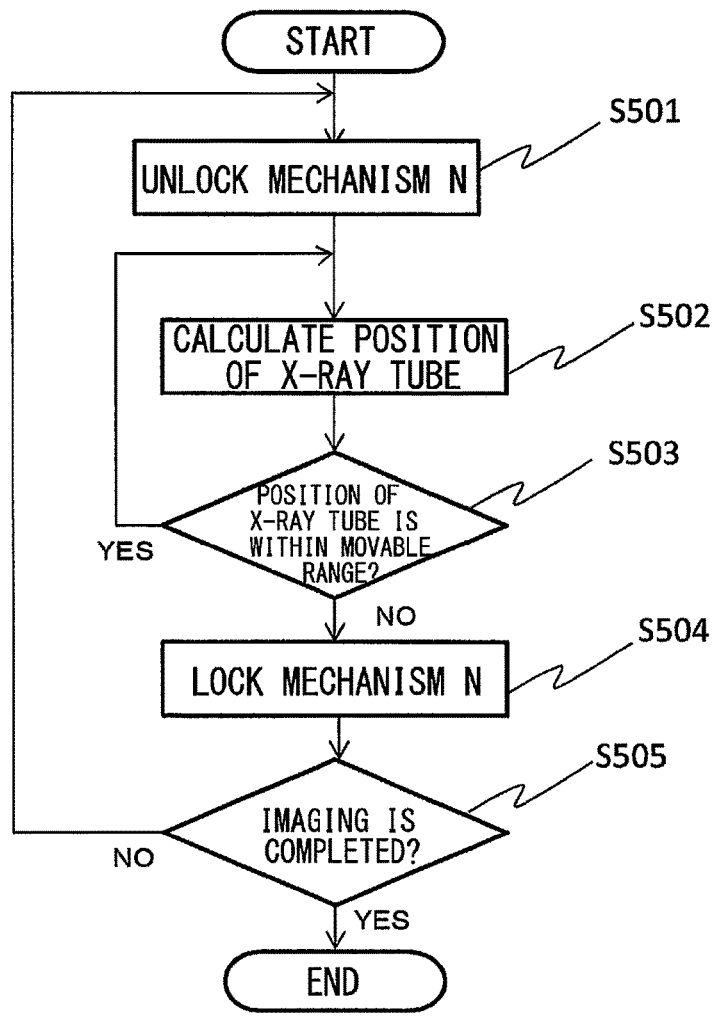
FIG. 16 illustrates operational procedures of the controller according to the second embodiment.

FIG. 16 illustrates an example of control procedure of the control unit 100. The example here will be described assuming that when one mechanism is in the movable state out of plural mechanisms for moving and rotating the arm unit, the other mechanisms are locked.

When the lock of any one of the plural mechanisms (mechanism N in the figure) is released and it is in the state of movable (S501), the control unit 100 calculates a position of the X-ray tube unit on the basis of information from the position detector (S502). It is determined whether the calculated position of the X-ray tube unit is within the movable range or not (S503), and if it is within the range, monitoring the position of the X-ray tube is continued. When the position of the X-ray tube unit exceeds the movable range, the mechanism N as to which the lock has been released, becomes locked (S504). If the X-ray tube unit needs to move (S505), the lock of the mechanisms other than the mechanism N is released (S501), the foregoing steps S502 to S504 are repeated. When the X-ray tube is set to a certain position, the operation for controlling the mechanisms is completed, and then imaging is started.

By way of example, when the end of the first arm 31 is positioned as indicated by the dotted lines as shown in FIG. 14($a$) and FIG. 14($b$), the angle $\theta$ of the first arm 31 and the angle $\varphi$ of the second arm are regulated in such a manner that the X-ray tube unit does not become lower than a predetermined level H and a distance from the front side of the main body does not become longer than the distance D.

As indicated by the solid line in FIG. 14($b$), when the end of the first arm 31 is positioned upwardly in the slide direction and the angle $\varphi$ of the second arm 32 is small, the angle $\theta$ of the first arm is regulated not to become smaller than a predetermined range, thereby avoiding collision of the X-ray tube unit 20 with the main body 10. On the other hand, as indicated by the dotted line, when the angle φ of the second arm 32 is large, the movable angle range of the first arm becomes larger, but the angle is regulated so that the X-ray tube unit 20 does not become equal to or lower than the predetermined level H.

According to the present embodiment, the control unit controls the operation of each mechanism on the basis of a predetermined movable range of the X-ray tube unit, whereby it is possible to prevent inadvertent collision of the X-ray tube unit 20 with the main body 10, and movement of the device to a position that may lose the balance of the device, when the position of the X-ray tube unit 20 is adjusted by moving plural mechanisms that are movable independently.

There has been described so far, the control of the mechanisms for moving the X-ray tube unit within the movable range. If a position detector for detecting the position of the X-ray detector is provided, the positional information of the X-ray detector, detected by the position detector, can be used to control the mechanisms so that the X-ray tube unit 20 is moved to a position facing the X-ray detector. As the position detector for detecting the position of the X-ray detector, a receiver set may be employed having the X-ray detector incorporating a transmitter, for specifying the position of the X-ray detector by receiving signals from the transmitter, or a position detector by utilizing magnetism or infrared radiation may be employed.

Third Embodiment

The present embodiment is based on the first embodiment and features that a balance mechanism is provided for balancing the X-ray imaging device, along with the movement of the X-ray tube. As the balance mechanism, there are provided, for example, a weight (balancer) and a mechanism for sliding the balancer in the horizontal direction, a mechanism for changing the inclination of wheels with respect to a vertical plane, and a mechanism for changing the inclination of the main body, and each of those mechanisms may be used alone, or in combination with one another.

In the present embodiment, there will be described the case where the balancer is provided.

The X-ray imaging device of the first embodiment incorporates a weighty element such as the power supply arranged within the main body 10, and thus even when a relatively weighty X-ray tube unit 20 is positioned outside the main body 10, the center of gravity is kept within the main body 10, thereby preventing unstable posture. However, the arm requires a predetermined length in order to secure flexibility of the imaging position, even when the main body 10 is downsized. Therefore, when the arm is extended and the position of the X-ray tube unit 20 is substantially away from the main body 10, the posture of the device may become unstable and topple over. The X-ray imaging device of the present embodiment is installed with a balancer that moves along with the movement of the X-ray tube, thereby stabilizing the posture.

Figure 17:
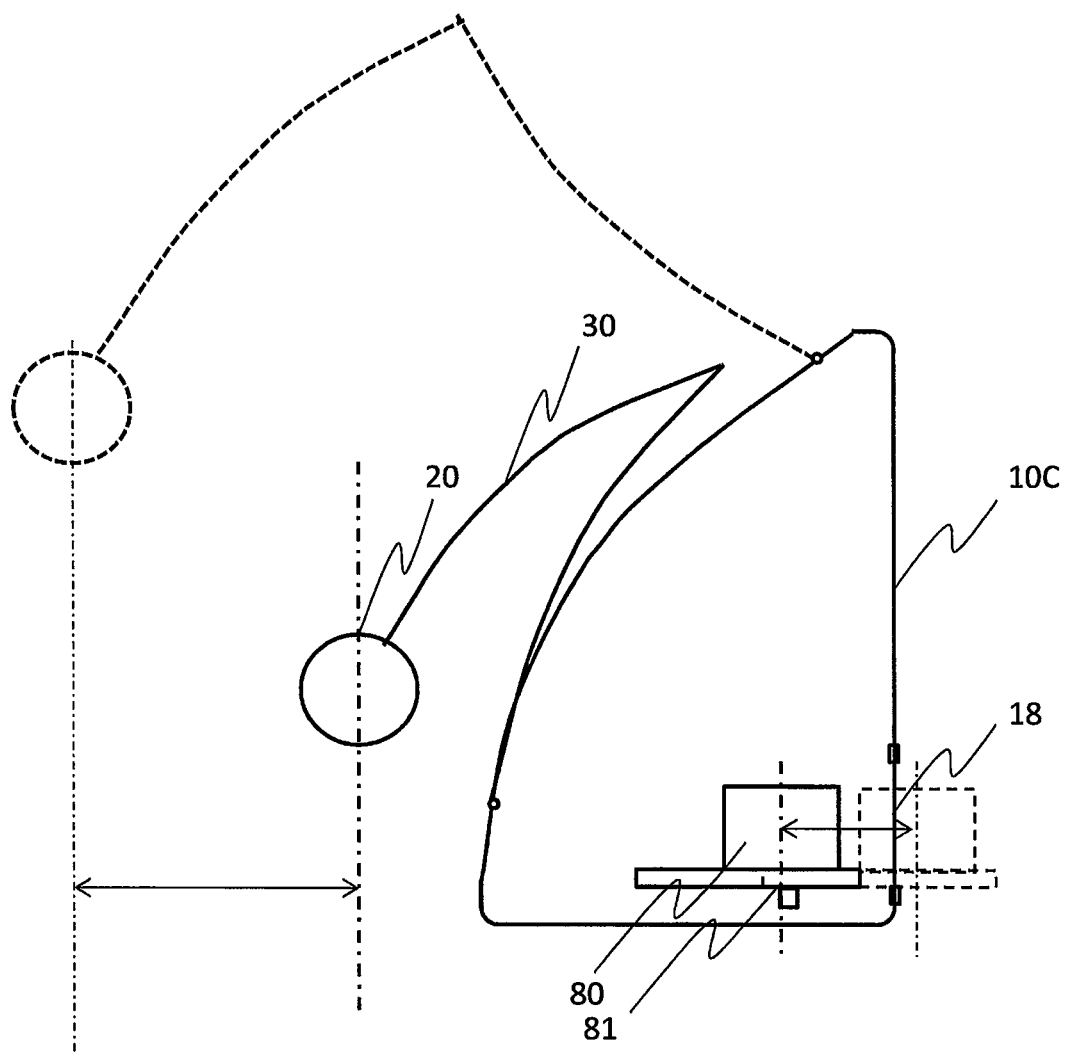
FIG. 17 illustrates a balancer of the mobile X-ray imaging device according to a third embodiment.
Figure 18:
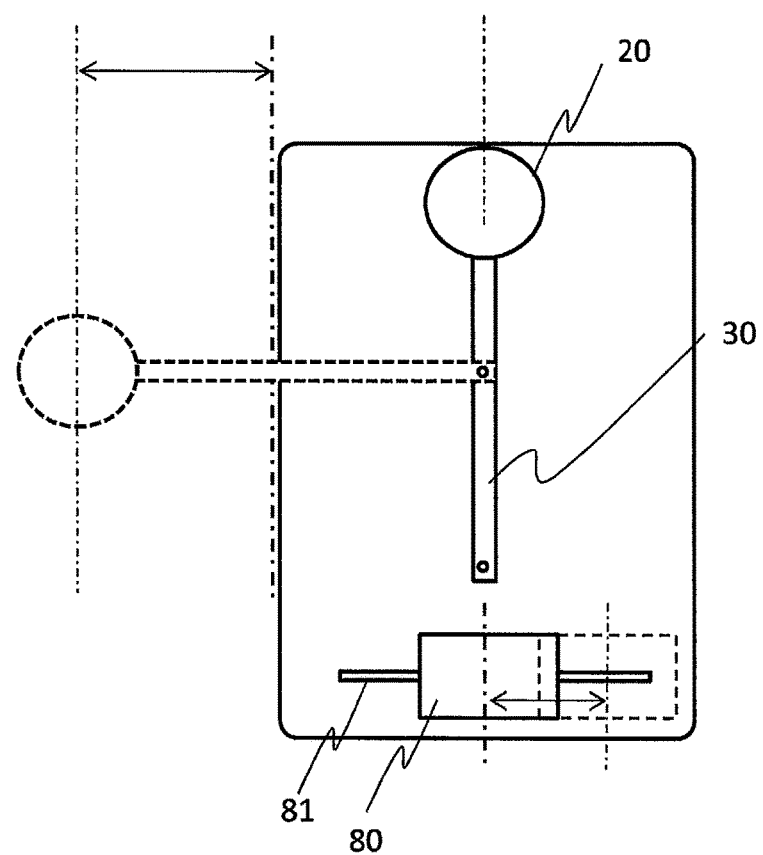
FIG. 18 illustrates the balancer of the mobile X-ray imaging device according to the third embodiment.

With reference to FIGS. 17 and 18, placement and operation of the balancer will be described. The configuration except the balancer is the same as the first embodiment, and redundant descriptions will not be provided. In addition, the same figures for describing the first embodiment will also be referred to, as required.

In the examples as shown in FIGS. 17 and 18, the balancer 80 is installed on a guide rail 81 in a rearward position on the bottom of the main body 10, the guide rail being configured to move the balancer 80 in the directions back and forth, and left and right. A weight made of a material of large specific gravity is used as the balancer. It is also possible to employ movable elements, among the elements such as the power supply accommodated within the main body enclosure, as a part or all of the balancer.

By way of example, a combination of Y rail and X-rail can be employed as the guide rail 81; the Y-rail being configured to move the balancer 80 in the back and forth directions, and the X-rail being configured to move the Y-rail in the left and right directions. In the example being illustrated, the X-rail is fixed within the main body 10, defining a moving range of the balancer 80 in the left and right directions. A guide for moving the Y-rail along the X-rail is fixed on the X-rail, and the Y-rail is movable in the Y-direction with respect to this guide. The balancer 80 is fixed on the Y-rail, and it moves together with the Y-rail. In the present embodiment, as for the Y-direction, the balancer 80 is movable to a position partially protruding from inside the main body 10. Therefore, there is provided an opening 18 on the back panel 10C of the main body 10 for putting in and taking out the balancer 80. It is of course possible to configure such that the balancer is moved back and forth within the main body 10, if a storage volume of the main body 10 is sufficiently large.

A drive source such as a motor enables the balancer 80 to move along the guide rail 81. The drive source may be incorporated in the balancer 80 itself and it is activated under the control of the control unit 100 (FIG. 13), so as to move the balancer 80 in a predetermined direction along the guide rail 81.

In the X-ray imaging device of the present embodiment, if the X-ray tube unit 20 is positioned within a predetermined range with respect to the main body 10, the balancer 80 does not move, but if the X-ray tube unit 20 moves exceeding the predetermined range, the balancer 80 is controlled to move. The predetermined range indicates that the center of gravity of the device falls into the range within the main body 10. The position of the X-ray tube unit 20 may be acquired from the position detector for detecting the position of the X-ray tube unit 20. Alternatively, the position of the X-ray tube unit 20 may be calculated, on the basis of the position of the end 311 of the first arm 31 along the slide mechanism and the first arm rotation angle (θ), the rotation angle (φ) of the second arm 32 with respect to the first arm, and the swiveling angle (ψ). Those angles above may be known according to the move amounts of the rotation mechanisms.

Figure 19:
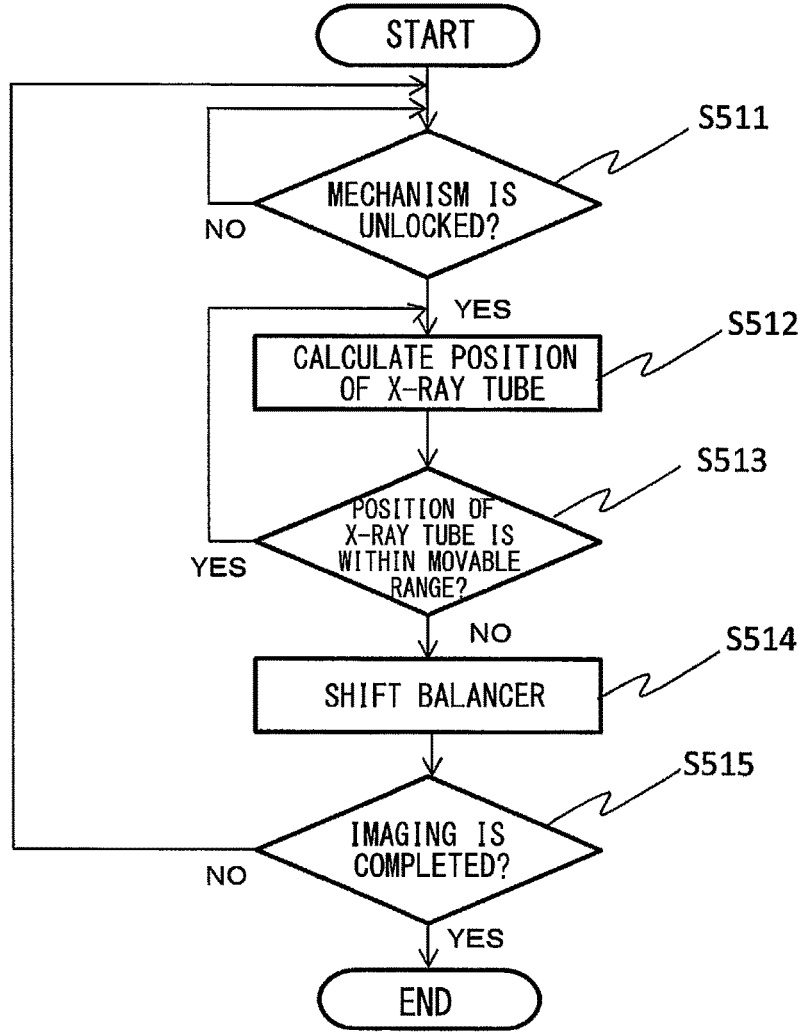
FIG. 19 illustrates operational procedures of the controller according to the third embodiment.

FIG. 19 shows one example of the control procedure of the control unit 100. When the lock of the mechanism is released and the arm unit is movable (S511), the control unit 100 calculates the position of the X-ray tube unit 20 based on the rotation angles, and the like, of the arms constituting the arm unit 30 as described above (S512). It is determined whether the position is within an allowable range (S513), and if the position exceeds the allowable range, the control unit transmits a signal to the drive source (not illustrated) of the balancer 80, so as to move the balancer 80 towards the side opposite to the direction in which the X-ray tube unit 20 exceeds the allowable range (S514). The move amount of the balancer 80 is determined according to a weight of the elements constituting the X-ray imaging device including the X-ray tube unit 20 and the balancer 80, in relation to the move amount to the X-ray tube unit 20, and it may be obtained in advance according to simulations, for instance. If imaging is performed by varying the position of the X-ray tube unit 20, the operation described above is repeated (S515).

FIG. 17 illustrates the situation that the balancer 80 is moved rearward, when the X-ray tube unit moves exceeding the forward allowable range. The forward allowable movable range is indicated by the dot-dash heavy line. FIG. 18 illustrates the situation that the balancer 80 is moved rightward, when the X-ray tube unit 20 is moved exceeding the left-side allowable range due to swiveling. In this figure, the allowable movable range corresponds to the range from the left end to the right end of main body 10, and only the left end is indicated by the dot-dash heavy line as a representative example. Similarly, when the center of the gravity moves rightward, the balancer 80 moves leftward.

In the present embodiment, the X-ray tube unit is not expected to be positioned rearward exceeding the back panel 10c of the main body 10. However, the X-ray tube unit 20 may be moved rearward, depending on the joint configuration of the arm unit. In that case, it is possible to employ a configuration, for example, the balancer 80 is moved forward, or a second balancer is placed in the forward of the power supply unit.

FIGS. 17 and 18 illustrate, respectively, the cases where the X-ray tube unit 20 moves forward, and moves leftward/rightward. It is of course possible, however, that movement of the X-ray tube unit 20 in the forward diagonal direction can be addressed by combining the movements of the balancer 80, in the left/right direction and in the forward direction.

According to the present embodiment, there is provided the balancer that shifts its location in conjunction with the movement of the X-ray tube, thereby mitigating a shift of the center of gravity due to downsizing of the device, and achieving posture stabilization.

Fourth Embodiment

In the third embodiment, the balancer is used to stabilize the posture of the X-ray imaging device. The present embodiment features that the posture of the device itself varies, so as to stabilize the posture.

Specifically, a mechanism for varying the height of the wheels mounted on the main body 10 is added, thereby stabilizing the posture, irrespective of the movement of the X-ray tube part 20.

Figure 20:
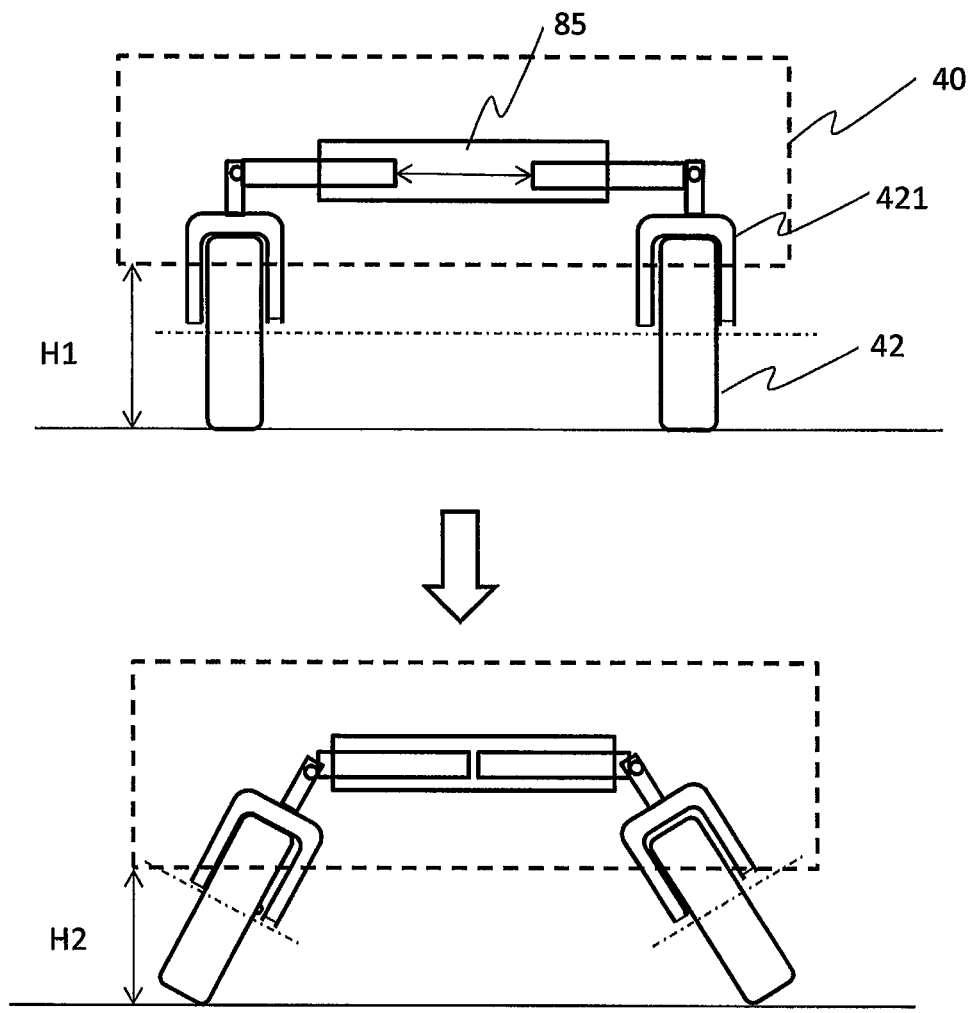
FIG. 20 illustrates one example of height adjustment mechanism of the mobile X-ray imaging device according to a fourth embodiment.

FIG. 20 illustrates one example of a height adjustment mechanism 85 provided on the rear wheels 42. The height adjustment mechanism 85 of this example is made up of a publicly known mechanism for generating linear power, such as a hydraulic cylinder, and it is fixed on the carriage 40 of the main body 10, so that the moving direction of a piston being a moving element of the mechanism becomes horizontal. The rear wheel 42 is supported at both ends, by a shaft supporter 421, so that the rotation axis becomes parallel to the horizontal direction, or the rotation axis forms a predetermined angle with the horizontal direction. The shaft supporter 421 has a u-shaped cross section, having the wheel placed between two ends, and the opposite-side end of the two ends, is coupled to the piston part of the height adjustment mechanism 85.

According to the height adjustment mechanism 85, when lateral power toward the center of the main body enclosure is applied to the top end of the shaft supporter 421, the rear wheel 42 is inclined while moving the contact surface with the floor outwardly, and the distance between the floor face and the main body 10 is made vary. That is, the height of the device is lowered (changed from H1 to H2). As illustrated, if the lateral power applied to both the rear wheels 42 is equivalent, the rear side of the device is lowered as a whole.

On the other hand, if the power is applied only to one of the left/right wheels 42, the one wheel 42 is inclined while the other wheel 42 is kept in almost the same state, resulting in that the device is inclined either to the left or to the right.

The height adjustment mechanism 85 is not limited to the mechanism as shown in FIG. 20. As far as the height of the main body is variable, any other mechanisms may be applicable, such as a mechanism for rotating the shaft supporter 421 so that the rear wheels 42 are inclined, and a mechanism that moves the shaft supporters 421 of the wheels in the vertical direction with respect to the main body, thereby varying the height of the main body with respect to the wheels.

The control unit 100 may control driving of the height adjustment mechanism 85 also in the present embodiment, on the basis of the positional information of the X-ray tube unit 20, similar to the driving of the balancer in the third embodiment. In other words, when the X-ray tube unit 20 moves rightward in the lateral direction of the main body 10, for example, and the center of gravity cannot be kept within the main body 10, the inclination of the left wheel 42 is made larger, thereby lowering the left side of the main body 10. Accordingly, the position of the center of gravity shifts to the left side, thereby keeping the center of gravity within the main body 10. On the other hand, when the X-ray tube unit 20 moves leftward, the inclination of the right wheel is made larger.

In the case where the X-ray tube unit 20 moves significantly forward, as indicated by the dotted line in FIG. 17, the inclination of the two rear wheels 42 is enlarged, whereby the center of gravity as a whole of the main body 10 is shifted downwardly, along with tilting the main body 10 so that the rear side thereof becomes lower.

As described above, a degree of inclination of the main body 10 with respect to the horizontal plane is made variable, along with the movement of the X-ray tube unit 20, thereby preventing the posture instability due to the move of the X-ray tube unit 20, and imaging with a stable posture can be achieved.

Embodiments of the mobile X-ray imaging device according to the present invention have been described so far, and those embodiments of the present invention can be combined as far as there is no structural inconsistency. In addition, any of the elements described in each of the embodiments may be omitted as appropriate, as far as it is not indispensable for the present invention, and such device is also included in the present invention.

INDUSTRIAL APPLICABILITY

According to the present invention, the mobile X-ray imaging device is provided, being superior in operability both in transit and upon imaging, and ensuring the device is prevented from toppling.

DESCRIPTION OF SYMBOLS

10 . . . main body, 10A . . . front panel, 10B . . . side panel, 10C . . . back panel, 11 . . . storage concave, 12 . . . opening (guide), 13 . . . X-ray tube storage, 15 . . . groove, 17 . . . X-ray detector storage, 19 . . . opening, 20 . . . X-ray tube unit, 21 . . . X-ray tube holder, 30 . . . arm unit, 31 to 35 . . . arm, 41 . . . front wheel, 42 . . . rear wheel, 50 . . . supporting from of X-ray detector, 51 . . . supporting member, 61 . . . display panel, 62 . . . display panel, 71 . . . transporting handle, 72 . . . arm operating handle, 73 . . . cover, 75, 76 . . . switch, 77, 78 . . . operation button, 80 ... balancer, 81 ... guide rail, 85 ... height adjustment mechanism, 100 ... control unit, 101 ... position calculator, 102 ... mechanism controller, 103 ... storage unit, 311, 312 ... end of the first arm, 313 ... wheel (axis), 321, 322 ... end of the second arm

What is claimed is:

1. A mobile X-ray imaging device comprising,
an X-ray tube unit,
a main body configured to accommodate a drive unit of the X-ray tube unit,
wheels mounted on the main body, and
an arm unit configured to connect the X-ray tube unit with the main body,
wherein the arm unit comprises a plurality of arms being foldable, and the main body has a storage concave for storing the arm unit being folded,
wherein the plurality of arms include a first arm and a second arm which is foldable with respect to the first arm, the first arm and the second arm being stored in the storage concave in a folded position and extending outside the storage concave in an unfolded position, and
wherein the first arm has one end which is slidably coupled to the storage concave and the second arm has one end which is attached to the X-ray tube unit.

2. The mobile X-ray imaging device according to claim 1, wherein the plurality of arms include a third arm having one end connected to the first arm and another end connected to the second arm, to be foldable with respect to with respect to the first arm and the third arm, and the X-ray tube unit is fixed to the end of the second arm.

3. The mobile X-ray imaging device according to claim 1, wherein the X-ray tube unit is fixed to the one end of the second arm.

4. The mobile X-ray imaging device according to claim 1, wherein,
the first arm has a shaft on the one end, and
the storage concave has a guide allowing the shaft to slide along a longitudinal direction of the storage concave.

5. The mobile X-ray imaging device according to claim 1 wherein the other end of the second arm is coupled to the other end of the first arm, in a manner rotatable about an axis orthogonal to the longitudinal direction of the second arm.

6. The mobile X-ray imaging device according to claim 1 wherein at least one of the first arm and the second arm comprises an expansion and contraction mechanism configured to expand and contract a length from one end to the other end.

7. The mobile X-ray imaging device according to claim 6, wherein the second arm includes an inside arm and an outside arm to form an expansion and contraction mechanism, the inside arm is attached to the X-ray tube, and the outside arm is coupled to the first arm, the outside arm having an inner space for accepting the inside arm, the inside arm fitting into the inner space and being inserted slidably therein along the longitudinal direction.

8. The mobile X-ray imaging device according to claim 1, wherein,
the main body comprises an inclined plane forward in a traveling direction, and the storage concave is provided on the inclined plane.

9. The mobile X-ray imaging device according to claim 8, wherein,
the inclined plane has a curved surface, the arms constituting the arm unit are curved along the curved surface of the inclined plane.

10. The mobile X-ray imaging device according to claim 1, further comprising a control unit configured to control movement of the arm unit.

11. The mobile X-ray imaging device according to claim 10, further comprising a detector configured to detect a position of the X-ray tube, wherein,
the control unit controls the movement of the arm unit, on the basis of the position of the X-ray tube detected by the detector.

12. The mobile X-ray imaging device according to claim 1, further comprising a balance mechanism configured to adjust the center of gravity balance of the mobile X-ray imaging device, in association with the movement of the arm unit.

13. The mobile X-ray imaging device according to claim 12, wherein,
the balance mechanism includes at least one of the following; a weight and a mechanism for sliding the weight in the horizontal direction, a mechanism for changing an angle of wheels with respect to a vertical plane, and a mechanism for changing an inclination of the main body.

14. The mobile X-ray imaging device according to claim 1, wherein the main body includes an X-ray tube storage configured to store the X-ray tube unit, adjacent to the storage concave or continuous therefrom.

15. The mobile X-ray imaging device according to claim 1, further comprising a support frame configured to support an X-ray detector that is used together with the mobile X-ray imaging device,
wherein grooves for storing the support frame are provided on both sides of the storage concave.

16. The mobile X-ray imaging device according to claim 15,
wherein the support frame comprises a link member that is slidable along the groove, and a support member that is foldable with respect to the link member.

17. The mobile X-ray imaging device according to claim 16,
wherein the support frame comprises two support members foldable with respect to two link members, and the two link members are inserted into the main body via two openings provided on the main body.

* * * * *